(12) United States Patent
Ito et al.

(10) Patent No.: US 6,294,183 B1
(45) Date of Patent: Sep. 25, 2001

(54) ANTIMICROBIAL RESIN COMPOSITION AND ANTIMICROBIAL RESIN MOLDED ARTICLE COMPRISING SAME

(75) Inventors: Takafumi Ito; Yasuo Matsumoto; Jun Hiraki, all of Yokohama (JP)

(73) Assignee: Chisso Corporation, Osaka (JP)

(*) Notice: Subject to any disclaimer, the term of this patent is extended or adjusted under 35 U.S.C. 154(b) by 0 days.

(21) Appl. No.: 09/242,719

(22) PCT Filed: Aug. 21, 1997

(86) PCT No.: PCT/JP97/02909

§ 371 Date: Feb. 22, 1999

§ 102(e) Date: Feb. 22, 1999

(87) PCT Pub. No.: WO98/07790

PCT Pub. Date: Feb. 26, 1998

(30) Foreign Application Priority Data

| Aug. 21, 1996 | (JP) | 8-238360 |
| Feb. 7, 1997 | (JP) | 9-040041 |
| Feb. 26, 1997 | (JP) | 9-058458 |
| Feb. 27, 1997 | (JP) | 9-060021 |
| May 8, 1997 | (JP) | 9-134354 |
| Aug. 15, 1997 | (JP) | 9-220441 |

(51) Int. Cl.$^7$ .......... A01N 25/34; A01N 25/00; A61K 38/00; A61K 31/165

(52) U.S. Cl. ............ 424/404; 424/405; 514/2; 514/619

(58) Field of Search .......... 424/402–405; 514/2, 619

(56) References Cited

U.S. PATENT DOCUMENTS

| 4,666,956 | * | 5/1987 | Spielau et al. | 523/122 |
| 5,236,645 | * | 8/1993 | Jones | 264/78 |

FOREIGN PATENT DOCUMENTS

| 62-286918 | 12/1987 | (JP) . |
| 1-222790 | 9/1989 | (JP) . |
| 2-20271 | 1/1990 | (JP) . |
| 4-13741 | 1/1992 | (JP) . |
| 4-53475 | 2/1992 | (JP) . |
| 5-68520 | 3/1993 | (JP) . |
| 5-170845 | 7/1993 | (JP) . |
| 6-206803 | 7/1994 | (JP) . |
| 6-346000 | 12/1994 | (JP) . |
| 8-170217 | 7/1996 | (JP) . |
| 9-132869 | 5/1997 | (JP) . |

* cited by examiner

Primary Examiner—Russell Travers
Assistant Examiner—Shengjun Wang
(74) Attorney, Agent, or Firm—Wenderoth, Lind & Ponack, L.L.P.

(57) ABSTRACT

The incorporation of $\epsilon$-polylysine or salt thereof ($\epsilon$PL) having a water content of not more than 15% by weight in a resin composition makes it possible to obtain an antibacterial resin composition excellent in antibacterial capacity and safe in use. Since the $\epsilon$PL can be fairly dispersed in the resin, the resulting molded article is not liable to destruction of external appearance. Accordingly, the antibacterial resin composition of the present invention can find good and wide application in medical sanitary goods, tableware, daily necessaries, automobile interior material, household appliance, film, sheet, fiber, coating compound such as paint, ink, and other goods which must be antibacterial. Further, the molded articles obtained from the resin composition according to the present invention can maintain its antibacterial effect even after repeated use and thus can be used over an extended period of time.

22 Claims, No Drawings

ANTIMICROBIAL RESIN COMPOSITION AND ANTIMICROBIAL RESIN MOLDED ARTICLE COMPRISING SAME

This application is a 371 of PCT/JP97/02909, filed Aug. 21, 1997, which claims the priority of JP8-238360, filed Aug. 21, 1996, JP9-040041, filed Feb. 7, 1997, JP9-058458, filed Feb. 26, 1997, JP9-060021, filed Feb. 27, 1997, JP9-134354, filed May 8, 1997, JP9-220441, filed Aug. 15, 1997.

TECHNICAL FIELD

The present invention relates to an antibacterial resin composition and a molded article obtained using the composition. More particularly, the present invention relates to an antibacterial resin composition comprising ε-polylysine or ε-polylysine salt (hereinafter generically referred to as "εPL") having a water content of not more than 15% by weight incorporated in a synthetic resin and to an antibacterial resin-molded article obtained from the composition.

BACKGROUND ART

Various bacteria and molds occur in our life space. These microorganisms often spoil foods or cause the generation of an offensive odor, offending us. Further, these microorganisms can cause diseases such as food poisoning or dermatopathy such as ringworm on the human body. Thus, the inhibition of proliferation of microorganism is an important subject for sanitary and comfortable life. It has been desired to provide our personal effects such as medical goods, daily necessaries and clothing with antibacterial capacity.

As a material of medical goods, daily necessaries, clothing, etc. there is used by preference a synthetic resin, which is light and rigid and can be freely molded to a desired shape. However, most synthetic resins have no antibacterial capacity themselves. In recent years, studies have been made on methods for imparting antibacterial function to synthetic resin-molded articles.

As a method for obtaining a synthetic resin-molded article having antibacterial capacity (hereinafter referred to as "antibacterial resin-molded article") there is disclosed a method of incorporating metals such as silver, copper and zinc in a synthetic resin in JP-A-54-147220 (The term "JP-A" as used herein means an "unexamined published Japanese patent application"). Further, JP-A-59-133235 discloses a method of incorporating a particulate zeolite-based solid matter ion-exchanged with silver ion or copper ion in a synthetic resin.

However, the antibacterial resin-molded article obtained by the method involving the incorporation of a metal-containing compound is disadvantageous in that it is liable to discoloration due to the metal compound incorporated therein and thus exhibits impaired external appearance and commercial value. Further, the antibacterial resin-molded article obtained by the method involving the incorporation of a particulate ion-exchanged zeolite-based solid matter in a synthetic resin is liable to production of chlorides by the reaction of metallic ions such as silver ion and copper ion with chlorine ion, if any, making it impossible to obtain a sufficient antibacterial capacity.

On the other hand, there is a method involving the incorporation of an antibacterial natural material which is little harm to the human body in a synthetic resin. Examples of such an antibacterial natural material include allyl isothiocyanate extracted from mustard or Japanese horse radish, protamine extracted from mature testis of salmon, trout, etc., and εPL obtained from microorganism belonging to streptomyces. A technique for the incorporation of a natural polylysine compound in a textile product is described in, e.g., JP-A-8-170217.

However, allyl isothiocyanate is disadvantageous in that it can vaporize readily during the molding of a resin composition and hence must be used in a large amount to render the resulting antibacterial resin-molded article fully antibacterial. Further, protamine is disadvantageous in that it is a protein and hence can be affected by heat too easily to withstand the processing temperature of the resin composition.

Among these natural antibacterial agents, εPL can exert an excellent antibacterial effect even when used in a small amount. Further, εPL can maintain its antibacterial effect even when heated to a temperature of from 200° C. to 250° C., which is required in the molding of a synthetic resin. εPL is normally used in the form of liquid composition obtained by mixing with ethanol as disclosed in JP-A-2-20271, liquid composition obtained by mixing with acetic acid as disclosed in JP-A-4-53475, powdery composition obtained by mixing an amino acid such as glycine as disclosed in JP-A-5-68520 or commercially available powdery composition obtained by mixing dextrin.

However, if such a composition is incorporated in a synthetic resin before molding to provide a resin-molded article with an antibacterial capacity, the resulting resin-molded article is liable to foaming.due to evaporation of solvent or burning of ingredients other than εPL, impairing the external appearance of the molded article or damaging the mold or roll. Further, εPL can be hardly dispersed uniformly in a resin, occasionally making it impossible to provide a sufficient antibacterial effect. Moreover, if the resin-molded article is adapted for use in environments requiring cleaning resistance, it is necessary to incorporate εPL in the resin in a high concentration, adding to the production cost.

Further, εPL is a substance having a high hydrophilicity and thus can be hardly dehydrated or dried. Therefore, normally available εPL has a high water content.

In general, εPL is mainly used as food additives or the like because of its effect. In these fields, the water content in εPL offers no special problem. In the previously mentioned field requiring the provision of a synthetic resin with an antibacterial capacity, however, the water content contained in εPL has an adverse effect on the moldability of the resin, causing molding defects or deterioration of the external appearance of the molded article. In particular, εPL having a high water content cannot be uniformly dispersed in a coating compound such as oil-based coating compound and printing ink. Further, such a coating compound or printing ink cannot be properly dried. Moreover, the resulting coat or printed matter exhibits an ill-developed color or a poor external coating or printing appearance.

DISCLOSURE OF THE INVENTION

The present invention has been made to solve the above-described problems. It is therefore an object of the present invention to provide an antibacterial resin composition which is little toxic to the human body, can exert a good antibacterial effect even when used in a small amount, can keep the resulting resin-molded article good in external appearance and can be cleaned in the form of molded article without deteriorating its continuous antibacterial capacity and an antibacterial resin-molded article such as medical sanitary goods, tableware, daily necessaries, automobile interior material, household appliance, film, sheet and fiber obtained from the antibacterial resin composition.

The inventors made extensive studies on an antibacterial resin composition which can exert a good antibacterial effect even when used in a small amount, can keep the resulting resin-molded article good in external appearance and can be cleaned in the form of molded article without deteriorating its continuous antibacterial capacity and an antibacterial resin-molded article obtained from the antibacterial resin composition. As a result, it was found that when an antibacterial resin composition obtained by incorporating εPL in a synthetic resin in an amount of not more than 15% by weight is molded, the resulting resin-molded article exhibits a drastic improvement in the dispersion of εPL therein and the elution of εPL therefrom. The present invention has been thus worked out based on this finding.

The present invention concerns antibacterial resin compositions and antibacterial resin-molded articles according to the following aspects 1 to 11.

1. An antibacterial resin composition comprising ε-polylysine or ε-polylysine salt (εPL) having a water content of not more than 15% by weight incorporated in a synthetic resin.

2. The antibacterial resin composition according to the above 1, wherein said ε-polylysine or ε-polylysine salt is obtained by a process which comprises subjecting an aqueous solution containing ε-polylysine or salt thereof to azeotropic treatment in the presence of an azeotropic agent to undergo dehydration followed by drying.

3. The antibacterial resin composition according to the above 1, wherein said ε-polylysine or ε-polylysine salt has an average particle diameter of not more than 200 μm.

4. The antibacterial resin composition according to the above 1, wherein the content of said ε-polylysine or ε-polylysine salt in said composition is from 0.001 to 10% by weight.

5. The antibacterial resin composition according to the above 1, wherein said ε-polylysine or ε-polylysine salt is supported on a carrier.

6. The antibacterial resin composition according to any one of the above 1 to 5, further comprising a surface active agent incorporated therein.

7. The antibacterial resin composition according to the above 6, wherein the mixing ratio of said ε-polylysine or ε-polylysine salt and said surface active agent is from 9:1 to 1:9 by weight.

8. The antibacterial resin composition according to the above 6 or 7, wherein said ε-polylysine or ε-polylysine salt is incorporated therein in admixture with said surface active agent.

9. The antibacterial resin composition according to any one of the above 1 to 6, further comprising a dispersant incorporated therein.

10. The antibacterial resin composition according to the above 9, wherein the mixing ratio of said ε-polylysine or ε-polylysine salt and said dispersant is from 100:1 to 1:100 by weight.

11. A molded article obtained using an antibacterial resin composition according to any one of the above 1 to 10.

BEST MODES FOR CARRYING OUT THE INVENTION

The present invention is described in detail below.

εPL used herein can be obtained by a process which comprises culturing Streptomyces albulus subspecies lisinopolymerus belonging to the genus Streptomyces, which is an εPL-producing bacteria described in, e.g., U.S. Pat. No. 1,245,361, in a culture medium, and then separating and withdrawing εPL from the resulting culture. The above-described εPL is a substance described in the list of existing additives filed by the Ministry of Public Welfare and is used as a food preservative, etc.

In the present invention, εPL may be used in free form or in the form of salt with an inorganic acid or organic acid (hereinafter generically referred to as "salt"). In either form, εPL shows no essential difference in antibacterial effect. However, εPL salt is faster to heat than free εPL. Therefore, if the resin is molded at a processing temperature of not lower than 230° C, εPL salt is preferably used.

Examples of εPL salt include salts of εPL with inorganic acids such as hydrochloric acid, sulfuric acid and phosphoric acid, organic acids such as acetic acid, propionic acid, fumaric acid, malic acid, citric acid, maleic acid, adipic acid and gluconic acid, medium-chain or long-chain saturated aliphatic acids such as caproic acid, lauric acid and stearic acid, and medium-chain and long-chain unsaturated aliphatic acid such as oleic acid, linoleic acid and arachidoic acid.

In the present invention, as an antibacterial agent for synthetic resin composition there is used εPL having a water content of not more than 15% by weight. If the water content exceeds 15% by weight, the molded article obtained by molding an antibacterial resin composition comprising a synthetic resin and such εPL is liable to drastic drop of dispersibility of εPL therein or foaming accompanied by molding failure. The lower limit of the water content in εPL is not specifically defined but is preferably not lower than 0.1% by weight. The smaller the water content in εPL is, the better is the moldability and dispersibility of εPL in the molded article. Thus, εPL having a water content of preferably from 0.05 to 8% by weight, more preferably from 0.1 to 6% by weight is preferably used in the present invention.

Such an εPL having a low water content can be produced by further dehydrating and drying an εPL obtained by an ordinary method over an extended period of time. Further, the use of a dehydration method such as heat-drying, vacuum drying, freeze drying and spray drying or a azeotropic dehydration method makes it possible to obtain an εPL having a water content of not more than 15% by weight.

In particular, the use of an azeotropic dehydration method makes it possible to obtain a high quality εPL having a water content of not more than 15% by weight according to the present invention at a low cost in a short period of time.

The term "azeotropic dehydration method" as used herein is meant to indicate a method which comprises mixing an aqueous solution of εPL with an azeotropic agent to obtain an azeotropic mixture comprising water and an azeotropic agent, and then heating the aqueous solution of εPL comprising an azeotropic mixture so that water content can be efficiently removed from the aqueous solution of εPL together with the azeotropic agent.

The term "azeotropic agent" as used herein is meant to indicate a material which can be mixed with an aqueous solution of εPL to produce an azeotropic mixture with water that can be evaporated to attain efficient removal of water content. Specific examples of the azeotropic agent employable herein include ethyl alcohol, isopropyl alcohol, butyl acetate, and toluene. However, any other substances may be used without any restriction so far as it can exert the above-described effect.

The azeotropic dehydration of the present invention may be accomplished by either a method which comprises heating an aqueous solution of εPL in the presence of an azeotropic agent at ordinary pressure to remove water content therefrom or a method which comprises removing water content from the aqueous solution of εPL under reduced pressure or in vacuo. In order to obtain an εPL having a low water content and impurity content in a short period of time at a low cost, it is preferred that the aqueous solution of εPL be subjected to azeotropic dehydration at a heating temperature of not higher than 60° C., more preferably not higher than 40° C.

In order to allow the azeotropic mixture to vaporize thoroughly, it is preferred that the azeotropic mixture thus azeotropically dehydrated be further subjected to drying.

For the drying of the azeotropic mixture, a widely used drying method such as heat drying, drying under reduced pressure and vacuum drying is enough. However, in order to obtain a high quality εPL, it is preferred that the azeotropic mixture be dried at a heating temperature of not higher than 60° C., more preferably not higher than 40° C.

The εPL obtained by azeotropic dehydration can provide a fragile solid matter as compared with εPL obtained by other dehydration and drying methods even if they have the same water content. Thus, the εPL thus obtained can be easily recovered after dried or can be easily atomized. Thus, the εPL thus obtained can be atomized to exhibit an enhanced dispersibility in an antibacterial resin-molded article, making it extremely easy to obtain an antibacterial resin-molded article having a good external appearance. Further, the εPL thus obtained exhibits a lower hygroscopicity after drying than εPL obtained by vacuum freeze drying and thus can maintain a low water content over an extended period of time.

In the present invention, by supporting εPL on a carrier, an εPL having a water content of not more than 15% by weight can be obtained. An εPL supported on a carrier is little liable to agglomeration of powder or sticking even when it absorbs water content such as moisture in the air and sweat from the operator, making it possible to improve handleability during addition to a synthetic resin.

The term "supported" as used herein is meant to indicate not only an arrangement comprising a supported material (εPL) physically, chemically or electrically bonded to a carrier but also an arrangement comprising a supported material merely attached to a carrier. From the standpoint of maintenance of antibacterial effect, it is preferred that the supported material be physically, chemically or electrically bonded to the carrier.

As the carrier on which εPL is supported in the present invention there may be used any inorganic or organic filler which is widely used for synthetic resins. The term "filler" as used herein is meant to indicate an inorganic or organic filler which is added to a synthetic resin for the purpose of improving the mechanical properties, function, heat resistance, etc. of synthetic resin-molded article or improving the moldability of the product or as an extender for increasing the volume of the product.

Preferred examples of inorganic fillers include silicate compounds such as silica gel, natural and synthetic zeolite and diatomaceous earth, talc, kaolin, hydrotalcite, calcium carbonate, phosphate compound and titanium oxide. Preferred examples of organic fillers include cellulose compounds, silicone resins, and activated carbon. Any other inorganic or organic fillers may be used depending on purpose so far as they do not impair the antibacterial effect of εPL.

If a filler having a negative charge on the surface thereof such as silica gel or a filler having a cation-exchanging capacity such as metal phosphate is used as an εPL carrier, it is electrically or ionically connected to εPL to restrict the rate of elution of εPL, making it possible to gradually release εPL over an extended period of time. Thus, an antibacterial agent which can maintain its antibacterial effect over an extended period of time can be obtained.

The filler comprising an εPL having a low water content supported thereon according to the present invention can be easily obtained by a process which comprises supporting an εPL uniformly on the surface of a filler, and then drying the supported material by a drying method properly selected from the group consisting of heat drying, vacuum drying, freeze drying and spray drying. Alternatively, a dehydration method by azeotropy with a solvent which helps dry single εPL such as ethyl alcohol and butyl acetate may be used. In the present invention, an εPL is supported on a filler. In this arrangement, the filler exerts a binding effect. Thus, the εPL can be more easily dried in this arrangement than in single form.

The amount of εPL to be supported on the filler is not specifically limited so far as it can be supported by the filler. In practice, however, the amount of εPL is preferably not more than 5 times that of the filler. In this arrangement, the εPL is little liable to agglomeration of powder or sticking due to moisture absorption and thus exhibits a good handleability during addition to the synthetic resin.

The εPL may be supported on the filler in combination with a surface active agent such as glycerinaliphatic acid ester and sucrose ester, an organic acid such as lactic acid, succinic acid, tartaric acid, fumaric acid, gluconic acid and adipic acid, and other substances which help the εPL to exert an antibacterial effect or give a synergim of an antibacterial effect (The εPL (ε-polylysine or salt thereof) and εPL supported on a carrier will be generically referred to as "εPL agent").

In the present invention, a particulate εPL agent having an average particle diameter of not more than 200 μm is preferably used. If an εPL agent having an average particle diameter of not more than 200 μm is used, the molded article obtained by molding an antibacterial synthetic resin composition comprising a synthetic resin and the above-described εPL agent has the above-described εPL agent dispersed more fairly therein. The smaller the particle diameter of the particulate εPL agent is, the better is the dispersibility of the εPL agent in the molded article. Thus, more preferably, a particulate εPL agent having an average particle diameter of from 0.1 to 100 μm, particularly from 1 to 50 μm, is used.

The particulate εPL agent can be easily prepared by using an existing grinding machine such as mortar, mill and grinder. In order that the effect of the present invention can be sufficiently exerted, it is preferred that the particulate εPL agent thus ground be sieved to uniformalize the particle diameter of the particulate εPL agent.

Examples of the synthetic resin to be used in the antibacterial resin composition of the present invention include polyolefinic resins such as binary or ternary copolymer of polypropylene and propylene with other α-olefins, low density polyethylene, linear low density polyethylene and high density polyethylene, thermoplastic polyester resins such as polyethylene terephthalate, polybutylene terephthalate and copolymer polyester, polyamide resins such as nylon 6 and nylon 66, polystyrene resins such as polystyrene and acrylonitrile-butadiene-styrene copolymer, thermoplastic resins such as vinyl chloride resin and vinylidene chloride resin, thermoplastic elastomers such as ethylenepropylene-rubber copolymer and styrene-butadiene-rubber copolymer, mixture thereof, and thermosetting resins such as unsaturated polyester resin, diallyl phthalate resin, phenol resin, epoxy resin and melamine-formaldehyde resin.

The antibacterial resin composition of the present invention comprises a coating compound and an ink incorporated therein. Examples of the synthetic resin to be used for the coating compound and ink include phenol resin, alkyd resin, melamine-alkyd resin, polyester resin, epoxy resin, polyurethane resin, vinyl acetate resin, styrene resin, acrylic resin, methacrylic resin, acrylsilicone resin, and fluororesin. The term "synthetic resin" as used herein includes urushi (Japanese lacquer), boiled oil, oil varnish and oil enamel, which essentially act in the same manner as synthetic resins when used with a coating compound and an ink, though being not synthetic resins generally speaking.

The process for the preparation of the antibacterial resin composition of the present invention is not specifically limited so far as a synthetic resin and an $\epsilon$PL having a water content of not more than 15% by weight are uniformly mixed.

The amount of $\epsilon$PL to be incorporated in the antibacterial resin composition is not specifically limited. In practice, however, the content of $\epsilon$PL in the antibacterial resin composition (content of pure $\epsilon$PL) is preferably from 0.001 to 10% by weight, more preferably from 0.01 to 5% by weight. When the content of $\epsilon$PL falls within the above defined range, a sufficient antibacterial effect can be exerted without impairing the external appearance and mechanical properties of the molded article.

The antibacterial resin composition of the present invention preferably further comprises various surface active agents and/or dispersants incorporated therein. When incorporated in a synthetic resin with an $\epsilon$PL agent, the surface active agents and/or dispersants exert an effect of remarkably changing the interfacial properties of the $\epsilon$PL agent and the synthetic resin at the interface of the two components. As a result, the microdispersibility of the $\epsilon$PL in the synthetic resin can be improved from the case where the $\epsilon$PL agent is singly added to the synthetic resin. Thus, the dispersion stability of the resin composition can be enhanced.

In the present invention, the synthetic resin may comprise a surface active agent and/or dispersant incorporated therein as mentioned above. The use of such a surface active agent and/or dispersant makes it possible to not only enhance the dispersibility of $\epsilon$PL agent in the synthetic resin and hence improve the antibacterial effect but also provide additive effects such as improvement in mechanical properties, surface gloss of molded article, smoothness and service slipperiness and provision of antistatic effect and wettability developed by functions inherent to the surface active agent and/or dispersant such as radical trapping effect and nucleating effect. Further, the use of a surface active agent and/or dispersant having an antibacterial effect allows the $\epsilon$PL and the surface active agent and/or dispersant to act on each other additively and synergistically, making it possible to obtain a synthetic resin composition more excellent in antibacterial effect.

Preferred examples of the surface active agent employable herein include polyvalent alcohol type nonionic surface active agents such as aliphatic acid ester of glycerin, aliphatic acid ester of sorbitol, aliphatic acid ester of sorbitan and alkyl glucoside, polyethylene glycol type nonionic surface active agents, betaine type amphoteric surface active agents, and quaternary ammonium salt type cationic surface active agents. These surface active agents are excellent particularly in the improvement in compatibility and dispersibility of $\epsilon$PL agent in the resin and the development of the antibacterial effect. Other surface active agents can be properly used depending on the purpose without impairing the antibacterial effect of $\epsilon$PL agent. The surface active agent of the present invention may be used in any form such as solid, powder, liquid and paste.

The surface active agent may be incorporated in the resin in the form of preparations obtained by uniformly mixing an $\epsilon$PL and a surface active agent at a proper ratio. Alternatively, the $\epsilon$PL agent and the surface active agent may be separately added.

The mixture of an $\epsilon$PL and a surface active agent may be in any form such as powder, liquid and paste so far as it has a water content of not more than 15% by weight.

The powdery mixture of an $\epsilon$PL and a surface active agent may be prepared by a method which comprises uniformly mixing a finely ground $\epsilon$PL and a finely ground surface active agent or a method which comprises uniformly dispersing an $\epsilon$PL and a surface active agent in a proper solvent such as water, drying the dispersion by a drying method such as vacuum drying, vacuum freeze drying and spray drying, and then finely dividing the resulting mixture by means of a grinding machine. A drying method requiring heating, if used, is preferably effected at a drying temperature of not higher than 60° C. to prevent the decomposition of the $\epsilon$PL and surface active agent.

The liquid or paste-like mixture of an $\epsilon$PL and a surface active agent may be prepared by a method which comprises uniformly mixing an $\epsilon$PL and a surface active agent or a method which comprises drying the mixture by a proper method such as vacuum drying and heat drying. A drying method requiring heating, if used, is preferably effected at a drying temperature of not higher than 60° C. to prevent the decomposition of the $\epsilon$PL and surface active agent.

The mixing ratio of the $\epsilon$PL agent and surface active agent to be used herein, i.e., the ratio of $\epsilon$PL agent:surface active agent is preferably from 9:1 to 1:9 by weight depending on the purpose.

Preferred examples of the dispersant employable herein include metal soap which is a salt of metal such as lithium, magnesium, calcium and zinc with an aliphatic acid such as stearic acid, lauric acid and oleic acid, hydrocarbon-based compound such as polyethylene wax and polypropylene wax, amide-based compound such as stearic acid amide and ethylenebisoleic acid amide, ester-based compound such as tristearic acid glycerol and phthalic acid dioctyl, and higher alcohol such as hexyl alcohol, heptyl alcohol, octyl alcohol and decyl alcohol. These dispersants are excellent particularly in the improvement in compatibility and dispersibility of $\epsilon$PL agent in the resin and the development of the antibacterial effect. Other dispersants employable herein are not specifically limited so far as they can exert the above-described effect.

The $\epsilon$PL agent and dispersant may be incorporated in the synthetic resin in the form of preparations obtained by uniformly mixing them at a proper ratio. Alternatively, the two components may be separately added to the synthetic resin.

The mixing ratio of the $\epsilon$PL agent and the dispersant to be used herein, i.e., the ratio of $\epsilon$PL agent:dispersant is preferably from 100:1 to 1:100, more preferably from 10:1 to 1:10 by weight, depending on the purpose.

In the present invention, the above-described surface active agent and the dispersant may be used in combination.

The antibacterial resin composition of the present invention may further comprise various additives commonly used in synthetic resins.

Examples of these additives include heat stabilizer for providing heat stability, heat deterioration resistance and heat resistance, weathering stabilizer for providing weathering resistance, light stabilizer for providing light resistance, various stabilizers for providing functions, neutralizer, additive, antistat, fog inhibitor, organic or inorganic pigment, and organic or inorganic filler for enhancing the mechanical strength of the molded article and providing functions. If necessary, an antibacterial aiding substance may be used to add to the antibacterial capacity of the εPL agent.

Referring to method for incorporating the εPL agent in a coating compound and an ink, the εPL agent, if it can be uniformly dispersed in the coating compound and ink, may be added to the coating compound and ink as it is or in the form of suspension in a proper solvent such as toluene, ethyl acetate and alcohol.

The process for preparing the antibacterial resin composition of the present invention is described below.

To the above-described synthetic resin is then added a mixture obtained by uniformly mixing an εPL and a surface active agent and/or dispersant at a proper ratio or an εPL agent and optionally a surface active agent and/or dispersant at a proper ratio in the resin. In this process, these components are added to the resin in an amount such that the concentration of εPL agent in the resin is preferably from 0.001 to 10% by weight, more preferably from 0.01 to 5% by weight. To the mixture may be added various additives commonly used in synthetic resins such as heat stabilizer for providing heat stability, heat deterioration resistance and heat resistance, weathering stabilizer for providing weathering resistance, light stabilizer for providing light resistance, various stabilizers for providing functions, additive, antistat, organic or inorganic pigment, organic or inorganic filler for enhancing the mechanical strength of the molded article and providing functions and antibacterial aiding substance for adding to the antibacterial capacity of εPL with stirring.

The composition comprising a thermoplastic resin can be obtained in pelletized form by a process which comprises heat-kneading the mixture thus stirred by means of a heat kneader such as screw extruder and roll, and then pelletizing the mixture thus kneaded.

In the present invention, the desired antibacterial resin-molded article can be obtained from the above-described antibacterial resin composition comprising an εPL agent having a water content of not more than 15% by weight.

As the process for obtaining the molded article there may be used any production process depending on the kind of the synthetic resin incorporated in the antibacterial resin composition. These production processes can be roughly divided into some groups, i.e., heat kneading process using an extruder, roll or the like as an ordinary process for molding thermoplastic resin and compression molding or extrusion as an ordinary process for molding thermosetting resin.

The molded article of the present invention may be obtained by molding an antibacterial resin composition comprising an εPL agent having a water content of not more than 15% by weight incorporated therein by means of a molding apparatus. Alternatively, the molded article of the present invention may be obtained by molding an antibacterial resin composition free of εPL agent with an εPL agent being added thereto inside or on a molding apparatus. In this process, the εPL agent may be used in the form of powder or may be heated so that it is used in the form of liquid.

Alternatively, a master batch prepared by adding an εPL agent having a water content of not more than 15% to a synthetic resin may be mixed with a synthetic resin composition free of εPL agent to obtain an antibacterial resin composition having a predetermined εPL agent concentration.

Further, in order to mold an antibacterial resin composition comprising a thermosetting resin, a prepolymer to be set may be mixed with the above-described filler preparations, various stabilizers, additives, pigments and fillers suitable for thermosetting resin, antibacterial aiding substance for adding to the antibacterial capacity of εPL and dispersant such as surface active agent for enhancing the dispersibility of filler preparations in the thermosetting resin, stirred, and then injected into a mold having a desired shape.

EXAMPLE

The present invention will be described in greater detail with reference to the following examples, but the invention should not be construed as being limited thereto. All the percents in the following Examples are by weight unless otherwise indicated.

<<Low Water Content εPL>>
(Production of Low Water Content εPL)
εPL-1

Into a 300 ml eggplant type flask was charged 150 ml of a 25% aqueous solution of εPL. The aqueous solution was then subjected to dehydration under reduced pressure at a heating temperature of 40° C. by means of a rotary evaporator until the volume of the liquid in the flask reached about 60 ml. To the residue was then added a guaranteed ethyl alcohol having a purity of 99.5% (hereinafter referred to as "ethanol") in an amount equal to that of the aqueous solution of εPL left in the flask. The mixture was then subjected to azeotropic dehydration at a heating temperature of 40° C. until the volume of the liquid in the flask reached about 60 ml. The above-described procedure was repeated three times. At the third azeotropic process, the operation was effected until ethanol was no longer confirmed evaporated from the flask. As a result, a semi-solid εPL was obtained. Subsequently, the εPL thus obtained was vacuum-dried in a vacuum dryer which had been adjusted to a heating temperature of 40° C. for 12 hours to remove the remaining ethanol content. Eventually, a solid εPL having a water content of 5.5% by weight was obtained (εPL-1).

εPL-2

The procedure of εPL-1 was followed except that the vacuum drying time was changed to 10 hours. As a result, a solid εPL having a water content of 7.9% by weight was obtained (εPL-2).

εPL-3

The procedure of εPL-1 was followed except that the vacuum drying time was changed to 6 hours. As a result, a solid εPL having a water content of 15.0% by weight was obtained (εPL-3).

εPL-4

Into a 300 ml eggplant type flask was charged 150 ml of a 25% aqueous solution of εPL. The aqueous solution of εPL was then subjected to azeotropic dehydration at a heating temperature of 40° C. until water was no longer confirmed evaporated from the flask. As a result, a semi-syrup-like εPL was obtained. Subsequently, the εPL thus obtained was vacuum-dried in a vacuum dryer which had been adjusted to a heating temperature of 40° C. for 12 hours to remove the remaining water content. Eventually, a solid εPL having a water content of 19.5% by weight was obtained (εPL-4).

(Test for measurement of water content)

The water content of the above-described εPL-1 to εPL-4 were measured in the following manner (heat loss method).

Using a microbalance capable of measuring 1/10 mg at minimum, εPL-1 to εPL-4 were each precisely measured out in an amount of 1 g. The sample was then heat-dried at a temperature of 105° C. for 60 minutes. The sample was immediately put in a desiccator containing silica gel where it was then allowed to stand at room temperature for 30 minutes. The sample was then again precisely measured out. The percent loss thus measured was defined as water content of the sample.

EXAMPLE 1

A polypropylene (MFR: 10 g/10 min, 230° C., 21.18N) and an εPL were uniformly mixed in a blender in such a manner that the amount of the polypropylene and the εPL were 99.0% and 1.0%, respectively. The mixture thus obtained was then packed into a mold having a size of 50 mm×50 mm×0.5 mm. The mold was then heat-compressed under a pressure of 19.61 MPa in a heat press which had been adjusted to 200° C. for 1 minute to prepare Polypropylene Sheet-1.

EXAMPLE 2

The procedure of Example 1 was followed except that εPL-2 was added in an amount of 1.0% instead of εPL-1 in an amount of 1.0%. As a result, Polypropylene Sheet-2 was prepared.

EXAMPLE 3

The procedure of Example 1 was followed except that εPL-3 was added in an amount of 1.0% instead of εPL-1 in an amount of 1.0%. As a result, Polypropylene Sheet-3 was prepared.

COMPARATIVE EXAMPLE 1

The procedure of Example 1 was followed except that εPL-4 was added in an amount of 1.0% instead of εPL-1 in an amount of 1.0%. As a result, Polypropylene Sheet-4 was prepared.

(Test 1 for Observation of External Appearance of Sheet)

Polypropylene Sheet-1 to 4 obtained in Examples 1 to 3 and Comparative Example 1 were visually observed for external appearance. The results are shown in Table 1 below.

TABLE 1

| Sample Name | | % Water content | External appearance of sheet by visual observation | Judgement |
|---|---|---|---|---|
| Example 1 | Polypropylene Sheet-1 | 5.5 | The dispersibility of εPL in the sheet and the smoothness of the sheet are good. The sheet is acceptable in external appearance. | ⊚ |
| Example 2 | Polypropylene Sheet-2 | 7.9 | The dispersibility of εPL in the sheet and the smoothness of the sheet are good. The sheet is acceptable in external appearance. | ○ |
| Example 3 | Polypropylene Sheet-3 | 15.0 | The dispersibility of εPL in the sheet is good. The sheet is acceptable in external appearance. | Δ |
| Comparative Example 1 | Polypropylene Sheet-4 | 19.5 | The dispersibility of εPL in the sheet is poor. Agglomerated εPL particles are observed in places. For external appearance, the sheet shows foaming, surface roughening and mottle. The sheet has a poor smoothness. | X |

⊚: Excellent external sheet appearance; judged applicable in wide application without any problem
○: Good external sheet appearance; judged applicable in many uses so far as high transparency and smoothness are not required
Δ: Slight poor external sheet appearance; judged difficultly applicable in uses requiring transparency and smoothness but applicable in uses requiring coloring
X: Poor external sheet appearance; judged inapplicable As can be seen in Table 1, the smaller the water content in εPL used is, the greater are the dispersibility of εPL in the polypropylene sheet and the smoothness of the polypropylene sheet. On the contrary, if the water content in εPL used exceeds 15%, the dispersibility of εPL in the polypropylene sheet is drastically deteriorated, and the polypropylene sheet shows foaming, surface roughening, mottle, etc., demonstrating that the smoothness and external appearance of the sheet are remarkably deteriorated.

EXAMPLE 4

The procedure of Example 1 was followed except that εPL-1 was added in an amount of 0.5% instead of 1.0%. As a result, Polypropylene Sheet-5 was prepared.

EXAMPLE 5

The procedure of Example 1 was followed except that εPL-3 was added in an amount of 0.5% instead of εPL-1 in an amount of 1.0%. As a result, Polypropylene Sheet-6 was prepared.

Comparative Example 2

The procedure of Example 1 was followed except that εPL-4 was added in an amount of 0.5% instead of εPL-1 in an amount of 1.0%. As a result, Polypropylene Sheet-7 was prepared.

EXAMPLE 6

The procedure of Example 1 was followed except that εPL-1 was added in an amount of 0.1% instead of 1.0%. As a result, Polypropylene Sheet-8 was prepared.

EXAMPLE 7

The procedure of Example 1 was followed except that εPL-3 was added in an amount of 0.1% instead of εPL-1 in an amount of 1.0%. As a result, Polypropylene Sheet-9 was prepared.

Comparative Example 3

The procedure of Example 1 was followed except that εPL-4 was added in an amount of 0.1% instead of εPL-1 in an amount of 1.0%. As a result, Polypropylene Sheet-10 was prepared.

EXAMPLE 8

The procedure of Example 1 was followed except that εPL-1 was added in an amount of 0.05% instead of 1.0%. As a result, Polypropylene Sheet-11 was prepared.

EXAMPLE 9

The procedure of Example 1 was followed except that εPL-3 was added in an amount of 0.05% instead of εPL-1 in an amount of 1.0%. As a result, Polypropylene Sheet-12 was prepared.

Comparative Example 4

The procedure of Example 1 was followed except that εPL-4 was added in an amount of 0.05% instead of εPL-1 in an amount of 1.0%. As a result, Polypropylene Sheet-13 was prepared.

Comparative Example 5

The procedure of Example 1 was followed except that εPL-1 was not added to obtain a nonbactericidal sample. As a result, Polypropylene Sheet-14 was prepared.
(Antibacterial effect test 1)

Specimens (50×50×0.5 mm) prepared from Polypropylene Sheet-1 and 3 to 14 obtained in Examples 1 and 3 to 9 and Comparative Examples 1 to 5 were each washed with flowing tap water at a rate of 2 l/min for 0 to 30 minutes. The specimen thus washed was then subjected to antibacterial effect test 1 in the following manner.
Antibacterial Testing Method (Film Contact Method)

The antibacterial effect test was conducted in accordance with "film contact method" defined as a synthetic resin antibacterial testing method in "Method for evaluation of antibacterial effect of inorganic antibacterial agents such as silver", Society for the Study of Inorganic Antibacterial Agents Such As Silver, 1995.
Preparation of Test Bacterial Liquid A nutrient broth was diluted with sterilized purified water 500 times to prepare a 1/500 medium having a pH value of 7.0±0.2. *Escherichia coli* (IFO3972) was then incubated in the growth medium through a sterilized pipette in an amount such that the viable cell count in the medium reached $3.0 \times 10^5$/ml.
Preparation of Specimen The specimen was lightly wiped with a pharmacopoeial gauze infiltrated with ethyl alcohol all over the entire surface thereof twice or three times, and then dried at room temperature before antibacterial effect test.
Antibacterial Effect Test These specimens were each put in a sterilized laboratory dish. The inoculum liquid was then incubated in the surface of the specimen in an amount of 0.5 ml. The specimen was then covered by a sterilized polyethylene coat film. The laboratory dish was then covered. The culture was grown at a temperature of 35±1° C. and a relative humidity of not lower than 90% for 24 hours. After the termination of growth, the specimen and cover film were thoroughly washed with SCDLP broth (10 ml) in such a manner that bacterial attached thereto were washed away into a sterilized laboratory dish. The wash liquid was then measured for viable cell count per ml by standard most probably number method. The measurements were then subjected to calculation for difference of increase or loss by the following equation. The results are shown in Table 2 below.
Nonbactericidal Sample

[A]: Viable cell count shortly after incubation

[B]: Viable cell count after a predetermined time of growth

Bactericidal Sample

[C]: Viable cell count after a predetermined time of growth

Difference of increase or loss=$\log_{10}$ (B/A)–$\log_{10}$ (C/A)

TABLE 2

| | Sample | % Added amount of εPL | % Water content | Difference of increase or loss | |
|---|---|---|---|---|---|
| | | | | Not washed | Washed with flowing water for 30 min. |
| Example 1 | Polypropylene Sheet-1 | 1.0 | 5.5 | 7.0 | 7.0 |
| Example 3 | Polypropylene Sheet-3 | 1.0 | 15.0 | 7.0 | 7.0 |
| Comparative Example 1 | Polypropylene Sheet-4 | 1.0 | 19.0 | 7.0 | 6.0 |
| Example 4 | Polypropylene Sheet-5 | 0.5 | 5.5 | 7.0 | 7.0 |
| Example 5 | Polypropylene Sheet-6 | 0.5 | 15.0 | 7.0 | 7.0 |
| Comparative Example 2 | Polypropylene Sheet-7 | 0.5 | 19.5 | 6.6 | 5.1 |
| Example 6 | Polypropylene Sheet-8 | 0.1 | 5.5 | 7.0 | 5.2 |
| Example 7 | Polypropylene Sheet-9 | 0.1 | 15.0 | 7.0 | 4.8 |
| Comparative Example 3 | Polypropylene Sheet-10 | 0.1 | 19.5 | 5.1 | 0 |
| Example 8 | Polypropylene Sheet-11 | 0.05 | 5.5 | 4.0 | 3.3 |
| Example 9 | Polypropylene Sheet-12 | 0.05 | 15.0 | 4.0 | 3.0 |
| Comparative Example 4 | Polypropylene Sheet-13 | 0.05 | 19.5 | 2.0 | 0 |
| Comparative Example 5 | Polypropylene Sheet-14 | 0 | Not added | 0 | 0 |

Name of bacteria: *Escherichia coli* (IFO3972)

As can be seen in Table 2, the specimens (comprising an εPL having a water content of not more than 15%) obtained in Examples 1 and 3 to 9 exert a high antibacterial effect on *Escherichia coli* as compared with the specimens (comprising an εPL having a water content of more than 15%) obtained in Comparative Examples 1 to 4 and the specimens (free of εPL) obtained in Comparative Example 5 and fairly maintain its antibacterial effect even after washing with flowing tap water for 30 minutes.

(Antibacterial Effect Test 2)

Specimens (50×50×0.5 mm) prepared from Polypropylene Sheet-1 and 3 to 14 obtained in Examples 1 and 3 to 9 and Comparative Examples 1 to 5 were each washed with flowing tap water at a rate of 2 l/min for 0 to 30 minutes. These specimens were each subjected to antibacterial effect test in the same manner as described in Test 1 except that as a testing bacteria there was used *Staphylococcus aureus* (IFO12732) instead of *Escherichia coli*. The results are shown in Table 3 below.

1.0%, respectively, based on 100% of the unsaturated polyester resin. The mixture was stirred to undergo uniform dissolution and dispersion, injected into a mold having a size of 50×50×0.5 mm, and then ripened at a temperature of 40° C. for 48 hours to prepare a sheet molding compound of unsaturated polyester resin. The sheet molding compound thus prepared was then heat-compressed under a pressure of 9.81 MPa in a heat press which had been adjusted to 150° C. for 15 minutes to prepare Unsaturated Polyester Sheet-1.

EXAMPLE 11

The procedure of Example 10 was followed except that εPL-2 was added in an amount of 1.0% instead of εPL-1 in an amount of 1.0%. As a result, Unsaturated Polyester Sheet-2 was prepared.

TABLE 3

| | | | | Difference of increase or loss | |
|---|---|---|---|---|---|
| | Sample | % Added amount of εPL | % Water content | Not washed | Washed with flowing water for 30 min. |
| Example 1 | Polypropylene Sheet-1 | 1.0 | 5.5 | 7.0 | 7.0 |
| Example 3 | Polypropylene Sheet-3 | 1.0 | 15.0 | 7.0 | 7.0 |
| Comparative Example 1 | Polypropylene Sheet-4 | 1.0 | 19.5 | 7.0 | 7.0 |
| Example 4 | Polypropylene Sheet-5 | 0.5 | 5.5 | 7.0 | 7.0 |
| Example 5 | Polypropylene Sheet-6 | 0.5 | 15.0 | 7.0 | 7.0 |
| Comparative Example 2 | Polypropylene Sheet-7 | 0.5 | 19.5 | 6.5 | 4.5 |
| Example 6 | Polypropylene Sheet-8 | 0.1 | 5.5 | 6.8 | 4.3 |
| Example 7 | Polypropylene Sheet-9 | 0.1 | 15.0 | 7.0 | 5.5 |
| Comparative Example 3 | Polypropylene Sheet-10 | 0.1 | 19.5 | 3.1 | 0 |
| Example 8 | Polypropylene Sheet-11 | 0.05 | 5.5 | 4.0 | 3.2 |
| Example 9 | Polypropylene Sheet-12 | 0.05 | 15.0 | 4.6 | 3.3 |
| Comparative Example 4 | Polypropylene Sheet-13 | 0.05 | 19.5 | 2.1 | 0 |
| Comparative Example 5 | Polypropylene Sheet-14 | 0 | Not added | 0 | 0 |

Name of bacteria: *Staphylococcus aureus* (IFO12732)

As can be seen in Table 3, the specimens (comprising an εPL having a water content of not more than 15%) obtained in Examples 1 and 3 to 9 exert a high antibacterial effect on *Staphylococcus aureus* as compared with the specimens (comprising an εPL having a water content of more than 15%) obtained in Comparative Examples 1 to 4 and the specimens (free of εPL) obtained in Comparative Example 5 and fairly maintain its antibacterial effect even after washing with flowing water for 30 minutes.

EXAMPLE 10

To Polylight PS-260M (unsaturated polyester resin produced by DAINIPPON INK & CHEMICALS, INC.) was added a styrene monomer in such an amount that the proportion of the unsaturated polyester resin reached 65% to obtain a liquid unsaturated polyester resin. Subsequently, to the unsaturated polyester resin were added a hardener, an accelerator and an εPL-1 in an amount of 1.2%, 5.0% and

EXAMPLE 12

The procedure of Example 10 was followed except that εPL-3 was added in an amount of 1.0% instead of εPL-1 in an amount of 1.0%. As a result, Unsaturated Polyester Sheet-3 was prepared.

Comparative Example 6

The procedure of Example 10 was followed except that εPL-4 was added in an amount of 1.0% instead of εPL-1 in an amount of 1.0%. As a result, Unsaturated Polyester Sheet-4 was prepared.

(Test 2 for Observation of External Appearance of Sheet)

Unsaturated Polyester Sheet-1 to 4 obtained in Examples 10 to 12 and Comparative Example 6 were visually observed for external appearance. The results are shown in Table 4 below.

TABLE 4

| Sample Name | | % Water content | External appearance of sheet by visual observation | Judgement |
|---|---|---|---|---|
| Example 10 | Unsaturated Polyester Sheet-1 | 5.5 | The dispersibility of εPL in the sheet and the smoothness of the sheet are good. The sheet is acceptable in external appearance. | ⊚ |
| Example 11 | Unsaturated Polyester Sheet-2 | 7.9 | The dispersibility of εPL in the sheet and the smoothness of the sheet are good. The sheet is acceptable in external appearance. | ○ |
| Example 12 | Unsaturated Polyester Sheet-3 | 15.0 | The dispersibility of εPL in the sheet is good. The sheet is acceptable in external appearance. | Δ |
| Comparative Example 6 | Unsaturated Polyester Sheet-4 | 19.5 | The dispersibiity of εPL in the sheet is poor. Agglomerated εPL particles are observed in places. For external appearance, the sheet shows foaming, surface roughening and mottle. The sheet has a poor smoothness. | × |

⊚: Excellent external sheet appearance; judged applicable in wide application without any problem
○: Good external sheet appearance; judged applicable in many uses so far as high transparency and smoothness are not required
Δ: Slight poor external sheet appearance; judged difficultly applicable in uses requiring transparency and smoothness but applicable in uses requiring coloring
×: Poor external sheet appearance; judged inapplicable As can be seen in Table 4, the smaller the water content in εPL used is, the greater are the dispersibility of εPL in the unsaturated polyester sheet and the smoothness of the unsaturated polyester sheet. On the contrary, if the water content in εPL used exceeds 15%, the dispersibility of εPL in the unsaturated polyester sheet is drastically deteriorated, and the unsaturated polyester sheet shows foaming, surface roughening, mottle, etc., demonstrating that the smoothness and external appearance of the sheet are remarkably deteriorated.

EXAMPLE 13

The procedure of Example 10 was followed except that εPL-1 was added in an amount of 0.5% instead of 1.0%. As a result, Unsaturated Polyester Sheet-5 was prepared.

EXAMPLE 14

The procedure of Example 10 was followed except that εPL-3 was added in an amount of 0.5% instead of εPL-1 in an amount of 1.0%. As a result, Unsaturated Polyester Sheet-6 was prepared.

Comparative Example 7

The procedure of Example 10 was followed except that εPL-4 was added in an amount of 0.5% instead of εPL-1 in an amount of 1.0%. As a result, Unsaturated Polyester Sheet-7 was prepared.

EXAMPLE 15

The procedure of Example 1 was followed except that εPL-1 was added in an amount of 0.1% instead of 1.0%. As a result, Unsaturated Polyester Sheet-8 was prepared.

EXAMPLE 16

The procedure of Example 10 was followed except that εPL-3 was added in an amount of 0.1% instead of εPL-1 in an amount of 1.0%. As a result, Unsaturated Polyester Sheet-9 was prepared.

Comparative Example 8

The procedure of Example 10 was followed except that εPL-4 was added in an amount of 0.1% instead of εPL-1 in an amount of 1.0%. As a result, Unsaturated Polyester Sheet-10 was prepared.

EXAMPLE 17

The procedure of Example 1 was followed except that ε-PL-1 was added in an amount of 0.05% instead of 1.0%. As a result, Unsaturated Polyester Sheet-11 was prepared.

EXAMPLE 18

The procedure of Example 10 was followed except that εPL-3 was added in an amount of 0.05% instead of εPL-1 in an amount of 1.0%. As a result, Unsaturated Polyester Sheet-12 was prepared.

Comparative Example 9

The procedure of Example 10 was followed except that εPL-4 was added in an amount of 0.05% instead of εPL-1 in an amount of 1.0%. As a result, Unsaturated Polyester Sheet-13 was prepared.

Comparative Example 10

The procedure of Example 10 was followed except that εPL-1 was not added to obtain a nonbactericidal sample. As a result, Unsaturated Polyester Sheet-14 was prepared.

(Antibacterial Effect Test 3)

The procedure of antibacterial effect test 1 was followed except that specimens (50×50×0.5 mm) prepared from Unsaturated Polyester Sheet-1 and 3 to 14 obtained in Examples 10 and 12 to 18 and Comparative Examples 6 to 10 were used instead of Polypropylene Sheet-1 and 3 to 14. The results are shown in Table 5 below.

TABLE 5

| | Sample | % Added amount of εPL | % Water content | Difference of increase or loss | |
|---|---|---|---|---|---|
| | | | | Not washed | Washed with flowing water for 30 min. |
| Example 10 | Unsaturated Polyester Sheet-1 | 1.0 | 5.5 | 7.0 | 7.0 |
| Example 12 | Unsaturated Polyester Sheet-3 | 1.0 | 15.0 | 7.0 | 7.0 |
| Comparative Example 6 | Unsaturated Polyester Sheet-4 | 1.0 | 19.5 | 7.0 | 7.0 |
| Example 13 | Unsaturated Polyester Sheet-5 | 0.5 | 5.5 | 7.0 | 7.0 |
| Example 14 | Unsaturated Polyester Sheet-6 | 0.5 | 15.0 | 7.0 | 7.0 |
| Comparative Example 7 | Unsaturated Polyester Sheet-7 | 0.5 | 19.5 | 5.5 | 4.0 |
| Example 15 | Unsaturated Polyester Sheet-8 | 0.1 | 5.5 | 6.0 | 4.8 |
| Example 16 | Unsaturated Polyester Sheet-9 | 0.1 | 15.0 | 6.6 | 6.1 |
| Comparative Example 8 | Unsaturated Polyester Sheet-10 | 0.1 | 19.5 | 3.1 | 0 |
| Example 17 | Unsaturated Polyester Sheet-11 | 0.05 | 5.5 | 4.2 | 3.2 |
| Example 18 | Unsaturated Polyester Sheet-12 | 0.05 | 15.0 | 4.3 | 3.2 |
| Comparative Example 9 | Unsaturated Polyester Sheet-13 | 0.05 | 19.5 | 2.3 | 0 |
| Comparative Example 10 | Unsaturated Polyester Sheet-14 | 0 | Not added | 0 | 0 |

Name of bacteria: *Escherichia coli* (IFO3972)

As can be seen in Table 5, the specimens (comprising an εPL having a water content of not more than 15%) obtained in Examples 10 and 12 to 18 exert a high antibacterial effect on *Escherichia coli* as compared with the specimens (comprising an εPL having a water content of more than 15%) obtained in Comparative Examples 6 to 9 and the specimens (free of εPL) obtained in Comparative Example 10 and fairly maintain its antibacterial effect even after washing with flowing water for 30 minutes.

(Antibacterial Effect Test 4)

The procedure of antibacterial effect test 2 was followed except that Unsaturated Polyester Sheet-1 and 3 to 14 obtained in Examples 10 and 12 to 18 and Comparative Examples 6 to 10 were used instead of Polypropylene Sheet-1 and 3 to 14. The results are shown in Table 6 below.

on *Staphylococcus aureus* as compared with the specimens (comprising an εPL having a water content of more than 15%) obtained in Comparative Examples 6 to 9 and the specimens (free of εPL) obtained in Comparative Example 10 and fairly maintain its antibacterial effect even after washing with flowing water for 30 minutes.

<<Finely Divided εPL>>

(Preparation of Finely Divided εPL)

The previously mentioned εPL-3 (solid εPL having a water content of 15.0%) was ground by means of a food mill (HL2053, produced by Phillips Corp.; hereinafter referred to as "food mill") for 10 seconds, and then passed through a wire sieve having a designated dimension of 1 mm defined in JIS Z8801-1987 to obtain εPL-5 in the form of fine powder. εPL-5 thus obtained was then measured for average particle diameter by laser analysis. The results were 350 μm.

TABLE 6

| | Sample | % Added amount of εPL | % Water content | Difference of increase or loss | |
|---|---|---|---|---|---|
| | | | | Not washed | Washed with flowing water for 30 min. |
| Example 10 | Unsaturated Polyester Sheet-1 | 1.0 | 5.5 | 7.0 | 7.0 |
| Example 12 | Unsaturated Polyester Sheet-3 | 1.0 | 15.0 | 7.0 | 7.0 |
| Comparative Example 6 | Unsaturated Polyester Sheet-4 | 1.0 | 19.5 | 7.0 | 7.0 |
| Example 13 | Unsaturated Polyester Sheet-5 | 0.5 | 5.5 | 7.0 | 7.0 |
| Example 14 | Unsaturated Polyester Sheet-6 | 0.5 | 15.0 | 7.0 | 7.0 |
| Comparative Example 7 | Unsaturated Polyester Sheet-7 | 0.5 | 19.5 | 6.5 | 5.0 |
| Example 15 | Unsaturated Polyester Sheet-8 | 0.1 | 5.5 | 7.0 | 4.8 |
| Example 16 | Unsaturated Polyester Sheet-9 | 0.1 | 15.0 | 7.0 | 5.5 |
| Comparative Example 8 | Unsaturated Polyester Sheet-10 | 0.1 | 19.5 | 3.1 | 0 |
| Example 17 | Unsaturated Polyester Sheet-11 | 0.05 | 5.5 | 4.0 | 3.3 |
| Example 18 | Unsaturated Polyester Sheet-12 | 0.05 | 15.0 | 4.1 | 3.3 |
| Comparative Example 9 | Unsaturated Polyester Sheet-13 | 0.05 | 19.5 | 1.1 | 0 |
| Comparative Example 10 | Unsaturated Polyester Sheet-14 | 0 | Not added | 0 | 0 |

Name of bacteria: *Staphylococcus aureus* (IFO12732)

As can be seen in Table 6, the specimens (comprising an εPL having a water content of not more than 15%) obtained in Examples 10 and 12 to 18 exert a high antibacterial effect

εPL-6

εPL-3 was ground by means of a food mill for 15 seconds, and then passed through a wire sieve having a designated dimension of 250 μm defined in JIS Z8801-1987 to obtain εPL-6 in the form of fine powder. εPL-6 thus obtained was then measured for average particle diameter by laser analysis. The results were 200 μm.

εPL-7

εPL-3 was ground by means of a food mill for 30 seconds, and then passed through a wire sieve having a designated dimension of 75 μm defined in JIS Z8801-1987 to obtain εPL-7 in the form of fine powder. εPL-7 thus obtained was then measured for average particle diameter by laser analysis. The results were 50 μm.

EXAMPLE 19

The procedure of Example 1 was followed except that εPL-7 was added in an amount of 1.0% instead of εPL-1 in an amount of 1.0%. As a result, Polypropylene Sheet-15 was prepared.

EXAMPLE 20

The procedure of Example 1 was followed except that εPL-6 was added in an amount of 1.0% instead of εPL-1 in an amount of 1.0%. As a result, Polypropylene Sheet-16 was prepared.

EXAMPLE 21

The procedure of Example 1 was followed except that εPL-5 was added in an amount of 1.0% instead of εPL-1 in an amount of 1.0%. As a result, Polypropylene Sheet-17 was prepared.

(Test 3 for Observation of External Appearance of Sheet)

Polypropylene Sheet-1 and 15 to 17 obtained in Examples 1 and 19 to 21 were visually observed for external appearance. The results are shown in Table 7 below.

As can be seen in Table 7, the smaller the water content in εPL used is, the greater are the dispersibility of εPL in the polypropylene sheet and the transparency and smoothness of the polypropylene sheet. Thus, a polypropylene sheet having the same external appearance as that comprising an εPL having a low water content (5.5%) can be obtained. In particular, if the average particle diameter of εPL used is not more than 200 μm, the resulting polypropylene sheet exhibits an excellent dispersibility of εPL and a good transparency and smoothness.

EXAMPLE 22

The procedure of Example 1 was followed except that εPL-7 was added in an amount of 0.5% instead of 1.0%. As a result, Polypropylene Sheet-18 was prepared.

EXAMPLE 23

The procedure of Example 1 was followed except that εPL-6 was added in an amount of 0.5% instead of εPL-7 in an amount of 1.0%. As a result, Polypropylene Sheet-19 was prepared.

EXAMPLE 24

The procedure of Example 1 was followed except that εPL-5 was added in an amount of 0.5% instead of εPL-7 in an amount of 1.0%. As a result, Polypropylene Sheet-20 was prepared.

EXAMPLE 25

The procedure of Example 1 was followed except that εPL-7 was added in an amount of 0.1% instead of 1.0%. As a result, Polypropylene Sheet-21 was prepared.

EXAMPLE 26

The procedure of Example 1 was followed except that εPL-6 was added in an amount of 0.1% instead of εPL-7 in an amount of 1.0%. As a result, Polypropylene Sheet-22 was prepared.

TABLE 7

| | Sample Name | Average particle diameter (μm) | % Water content | External appearance of sheet by visual observation | Judgement |
| --- | --- | --- | --- | --- | --- |
| Example 19 | Polypropylene Sheet-15 | 50 | 15.0 | The dispersibility of εPL in the sheet and the smoothness of the sheet are extremely good. The sheet is acceptable in external appearance. | ⊚ |
| Example 20 | Polypropylene Sheet-16 | 200 | 15.0 | The dispersibility of εPL in the sheet and the smoothness of the sheet are good. The sheet is acceptable in external appearance. | ○ |
| Example 21 | Polypropylene Sheet-17 | 350 | 15.0 | The dispersibility of εPL in the sheet is good. The sheet is acceptable in external appearance. | Δ |
| Example 1 | Polypropylene Sheet-1 | | 5.5 | The dispersibility of εPL in the sheet and the smoothness of the sheet are good. The sheet is acceptable in external appearance. | ⊚ |

⊚ : Excellent external sheet appearance; judged applicable in wide application without any problem
○ : Good external sheet appearance; judged applicable in many uses so far as high transparency and smoothness are not required
Δ: Slight poor external sheet appearance; judged difficultly applicable in uses requiring transparency and smoothness but applicable in uses requiring coloring
×: Poor external sheet appearance; judged inapplicable

EXAMPLE 27

The procedure of Example 1 was followed except that εPL-5 was added in an amount of 0.1% instead of εPL-7 in an amount of 1.0%. As a result, Polypropylene Sheet-23 was prepared.

EXAMPLE 28

The procedure of Example 1 was followed except that εPL-7 was added in an amount of 0.05% instead of 1.0%. As a result, Polypropylene Sheet-24 was prepared.

EXAMPLE 29

The procedure of Example 1 was followed except that εPL-6 was added in an amount of 0.05% instead of εPL-7 in an amount of 1.0%. As a result, Polypropylene Sheet-25 was prepared.

EXAMPLE 30

The procedure of Example 1 was followed except that εPL-5 was added in an amount of 0.05% instead of εPL-7 in an amount of 1.0%. As a result, Polypropylene Sheet-26 was prepared.

(Antibacterial Effect Test 5)

The procedure of antibacterial effect test 1 was followed except that Polypropylene Sheet-1, 5, 8, 11 and 14 to 26 obtained in Examples 1, 4, 6, 8 and 19 to 30 and Comparative Example 5 were used instead of Polypropylene Sheet-1 and 3 to 14. The results are shown in Table 8 below.

As can be seen in Table 8, the specimens obtained in Examples 19 to 30 exert a sufficient antibacterial effect as compared with the specimens (free of εPL) obtained in Comparative Example 5. In particular, the specimens comprising an εPL having an average particle diameter of not more than 200 μm incorporated therein, despite its water content of 15.0% in εPL, exert the same antibacterial effect on *Escherichia coli* as the specimens (comprising an εPL having a water content of 5.5% incorporated therein) obtained in Examples 1, 4, 6 and 8, which exert an excellent antibacterial effect in Antibacterial effect test 1. In some detail, these specimens exert a high antibacterial effect on *Escherichia coli* as compared with the specimens (comprising an εPL having an average particle diameter of more than 200 μm incorporated therein) obtained in Examples 21, 24, 27 and 30 and fairly maintain its antibacterial effect even after washing with flowing water for 30 minutes.

(Antibacterial Effect Test 6)

The procedure of antibacterial effect test 2 was followed except that Polypropylene Sheet-1, 5, 8, 11 and 14 to 26 obtained in Examples 1, 4, 6, 8 and 19 to 30 and Comparative Example 5 were used instead of Polypropylene Sheet-1 and 3 to 14. The results are shown in Table 9 below.

TABLE 8

| | Sample | % Added amount of εPL | Average particle diameter (μm) | % Water content | Difference of increase or loss | |
|---|---|---|---|---|---|---|
| | | | | | Not washed | Washed with flowing water for 30 min. |
| Example 19 | Poly-propylene Sheet-15 | 1.0 | 50 | 15.0 | 7.0 | 7.0 |
| Example 20 | Poly-propylene Sheet-16 | 1.0 | 200 | 15.0 | 7.0 | 7.0 |
| Example 21 | Poly-propylene Sheet-17 | 1.0 | 350 | 15.0 | 7.0 | 5.8 |
| Example 22 | Poly-propylene Sheet-18 | 0.5 | 50 | 15.0 | 7.0 | 7.0 |
| Example 23 | Poly-propylene Sheet-19 | 0.5 | 200 | 15.0 | 7.0 | 7.0 |
| Example 24 | Poly-propylene Sheet-20 | 0.5 | 350 | 15.0 | 5.5 | 4.2 |
| Example 25 | Poly-propylene Sheet-21 | 0.1 | 50 | 15.0 | 7.0 | 7.0 |
| Example 26 | Poly-propylene Sheet-22 | 0.1 | 200 | 15.0 | 6.0 | 4.8 |
| Example 27 | Poly-propylene Sheet-23 | 0.1 | 350 | 15.0 | 4.0 | 2.5 |
| Example 28 | Poly-propylene Sheet-24 | 0.05 | 50 | 15.0 | 5.2 | 3.3 |
| Example 29 | Poly-propylene Sheet-25 | 0.05 | 200 | 15.0 | 4.0 | 3.0 |
| Example 30 | Poly-propylene Sheet-26 | 0.05 | 350 | 15.0 | 3.3 | 2.0 |
| Example 1 | Poly-propylene Sheet-1 | 1.0 | | 5.5 | 7.0 | 7.0 |
| Example 4 | Poly-propylene Sheet-5 | 0.5 | | 5.5 | 7.0 | 7.0 |
| Example 6 | Poly-propylene Sheet-8 | 0.1 | | 5.5 | 7.0 | 5.2 |
| Example 8 | Poly-propylene Sheet-11 | 0.05 | | 5.5 | 4.0 | 3.3 |
| Comparative Example 5 | Poly-propylene Sheet-14 | 0 | | Not added | 0 | 0 |

Name of bacteria: *Escherichia coli* (IFO3972)

TABLE 9

| | Sample | % Added amount of εPL | Average particle diameter (μm) | % Water content | Difference of increase or loss | |
|---|---|---|---|---|---|---|
| | | | | | Not washed | Washed with flowing water for 30 min. |
| Example 19 | Poly-propylene Sheet-15 | 1.0 | 50 | 15.0 | 7.0 | 7.0 |
| Example 20 | Poly-propylene Sheet-16 | 1.0 | 200 | 15.0 | 7.0 | 7.0 |
| Example 21 | Poly-propylene Sheet-17 | 1.0 | 350 | 15.0 | 6.9 | 6.0 |
| Example 22 | Poly-propylene Sheet-18 | 0.5 | 50 | 15.0 | 7.0 | 7.0 |
| Example 23 | Poly-propylene Sheet-19 | 0.5 | 200 | 15.0 | 7.0 | 7.0 |
| Example 24 | Poly-propylene Sheet-20 | 0.5 | 350 | 15.0 | 5.5 | 4.0 |
| Example 25 | Poly-propylene Sheet-21 | 0.1 | 50 | 15.0 | 7.0 | 7.0 |
| Example 26 | Poly-propylene Sheet-22 | 0.1 | 200 | 15.0 | 3.7 | 5.5 |
| Example 27 | Poly-propylene Sheet-23 | 0.1 | 350 | 15.0 | 7.0 | 5.5 |
| Example 28 | Poly-propylene Sheet-24 | 0.05 | 50 | 15.0 | 5.2 | 3.5 |
| Example 29 | Poly-propylene Sheet-25 | 0.05 | 200 | 15.0 | 4.6 | 3.3 |
| Example 30 | Poly-propylene Sheet-26 | 0.05 | 350 | 15.0 | 3.5 | 2.2 |
| Example 1 | Poly-propylene Sheet-1 | 1.0 | | 5.5 | 7.0 | 7.0 |
| Example 4 | Poly-propylene Sheet-5 | 0.5 | | 5.5 | 7.0 | 7.0 |
| Example 6 | Poly-propylene Sheet-8 | 0.1 | | 5.5 | 6.8 | 4.3 |
| Example 8 | Poly-propylene Sheet-11 | 0.05 | | 5.5 | 4.0 | 3.2 |
| Comparative Example 5 | Poly-propylene Sheet-14 | 0 | | Not added | 0 | 0 |

Name of bacteria: *Staphylococcus aureus* (IFO12732)

As can be seen in Table 9, the specimens obtained in Examples 19 to 30 exert a sufficient antibacterial effect as compared with the specimens (free of εPL) obtained in Comparative Example 5. In particular, the specimens comprising an εPL having an average particle diameter of not more than 200 μm incorporated therein, despite its water content of 15.0% in εPL, exert the same antibacterial effect on *Staphylococcus aureus* as the specimens (comprising an εPL having a water content of 5.5% incorporated therein) obtained in Examples 1, 4, 6 and 8, which exert an excellent antibacterial effect in Antibacterial effect test 2. In some detail, these specimens exert a high antibacterial effect on *Staphylococcus aureus* as compared with the specimens (comprising an εPL having an average particle diameter of more than 200 μm incorporated therein) obtained in Examples 21, 24, 27 and 30 and fairly maintain its antibacterial effect even after washing with flowing water for 30 minutes.

EXAMPLE 31

The procedure of Example 10 was followed except that εPL-7 was added in an amount of 1.0% instead of εPL-1 in an amount of 1.0%. As a result, Unsaturated Polyester Sheet-15 was prepared.

EXAMPLE 32

The procedure of Example 10 was followed except that εPL-6 was added in an amount of 1.0% instead of εPL-1 in an amount of 1.0%. As a result, Unsaturated Polyester Sheet-16 was prepared.

EXAMPLE 33

The procedure of Example 10 was followed except that εPL-5 was added in an amount of 1.0% instead of εPL-1 in an amount of 1.0%. As a result, Unsaturated Polyester Sheet-17 was prepared.

(Test 4 for Observation of External Appearance of Sheet)

Unsaturated Polyester Sheet-1 and 15 to 17 obtained in Examples 10 and 31 to 33 were visually observed for external appearance. The results are shown in Table 10 below.

TABLE 10

| | Sample Name | Average particle diameter (μm) | % Water content | External appearance of sheet by visual observation | Judgement |
|---|---|---|---|---|---|
| Example 31 | Unsaturated Polyester Sheet-15 | 50 | 15.0 | The dispersibility of εPL in the sheet and the smoothness of the sheet are extremely good. The sheet is acceptable in external appearance. | ⊙ |
| Example 32 | Unsaturated Polyester Sheet-16 | 200 | 15.0 | The dispersibility of εPL in the sheet and the smoothness of the sheet are extremely good. The sheet is acceptable in external appearance. | ○ |
| Example 33 | Unsaturated Polyester Sheet-17 | 350 | 15.0 | The dispersibility of εPL in the sheet is good. The sheet is acceptable in external appearance. | Δ |
| Example 10 | Unsaturated Polyester Sheet-1 | | 5.5 | The dispersibility of εPL in the sheet and the smoothness of the sheet are extremely good. The sheet is acceptable in external appearance. | ⊙ |

TABLE 10-continued

| Sample Name | Average particle diameter (μm) | % Water content | External appearance of sheet by visual observation | Judgement |
|---|---|---|---|---|

⊚ : Excellent external sheet appearance; judged applicable in wide application without any problem
○ : Good external sheet appearance; judged applicable in many uses so far as high transparency and smoothness are not required
Δ: Slight poor external sheet appearance; judged difficultly applicable in uses requiring transparency and smoothness but applicable in uses requiring coloring
×: Poor external sheet appearance; judged inapplicable As can be seen in Table 10, the smaller the water content in εPL used is, the greater are the dispersibility of εPL in the unsaturated polyester sheet and the transparency and smoothness of the unsaturated polyester sheet. Thus, an unsaturated polyester sheet having the same external appearance as that comprising an εPL having a low water content (5.5%) can be obtained. In particular, if the average particle diameter of εPL used is not more than 200 μm, the resulting unsaturated polyester sheet exhibits an excellent dispersibility of εPL and a good transparency and smoothness free from surface roughening, mottle, etc.

EXAMPLE 34

The procedure of Example 10 was followed except that εPL-7 was added in an amount of 0.5% instead of 1.0%. As a result, Polypropylene Sheet-18 was prepared.

EXAMPLE 35

The procedure of Example 10 was followed except that εPL-6 was added in an amount of 0.5% instead of εPL-7 in an amount of 1.0%. As a result, Polypropylene Sheet-19 was prepared.

EXAMPLE 36

The procedure of Example-10 was followed except that εPL-5 was added in an amount of 0.5% instead of εPL-7 in an amount of 1.0%. As a result, Polypropylene Sheet-20 was prepared.

EXAMPLE 37

The procedure of Example 10 was followed except that εPL-7 was added in an amount of 0.1% instead of εPL-7 in an amount of 1.0%. As a result, Polypropylene Sheet-21 was prepared.

EXAMPLE 38

The procedure of Example 10 was followed except that εPL-6 was added in an amount of 0.1% instead of εPL-7 in an amount of 1.0%. As a result, Polypropylene Sheet-22 was prepared.

EXAMPLE 39

The procedure of Example 10 was followed except that εPL-5 was added in an amount of 0.1% instead of εPL-7 in an amount of 1.0%. As a result, Polypropylene Sheet-23 was prepared.

EXAMPLE 40

The procedure of Example 10 was followed except that εPL-7 was added in an amount of 0.05% instead of 1.0%. As a result, Polypropylene Sheet-24 was prepared.

EXAMPLE 41

The procedure of Example 10 was followed except that εPL-6 was added in an amount of 0.05% instead of εPL-7 in an amount of 1.0%. As a result, Polypropylene Sheet-25 was prepared.

EXAMPLE 42

The procedure of Example 10 was followed except that εPL-5 was added in an amount of 0.05% instead of εPL-7 in an amount of 1.0%. As a result, Polypropylene Sheet-26 was prepared.

(Antibacterial Effect Test 7)

The procedure of antibacterial effect test 1 was followed except that Unsaturated Polyester Sheet-1, 5, 8, 11 and 14 to 26 obtained in Examples 10, 13, 15, 17 and 31 to 42 and Comparative Example 10 were used instead of Polypropylene Sheet-1 and 3 to 14. The results are shown in Table 11 below.

TABLE 11

| | Sample | % Added amount of εPL | Average particle diameter (μm) | % Water content | Difference of increase or loss | |
|---|---|---|---|---|---|---|
| | | | | | Not washed | Washed with flowing water for 30 min. |
| Example 31 | Poly-propylene Sheet-15 | 1.0 | 50 | 15.0 | 7.0 | 7.0 |
| Example 32 | Poly-propylene Sheet-16 | 1.0 | 200 | 15.0 | 7.0 | 7.0 |
| Example 33 | Poly-propylene Sheet-17 | 1.0 | 350 | 15.0 | 7.0 | 5.8 |
| Example 34 | Poly-propylene Sheet-18 | 0.5 | 50 | 15.0 | 7.0 | 7.0 |
| Example 35 | Poly-propylene Sheet-19 | 0.5 | 200 | 15.0 | 7.0 | 7.0 |
| Example 36 | Poly-propylene Sheet-20 | 0.5 | 350 | 15.0 | 5.5 | 4.2 |
| Example 37 | Poly-propylene Sheet-21 | 0.1 | 50 | 15.0 | 7.0 | 7.0 |
| Example 38 | Poly-propylene Sheet-22 | 0.1 | 200 | 15.0 | 6.0 | 4.8 |
| Example 39 | Poly-propylene Sheet-23 | 0.1 | 350 | 15.0 | 4.0 | 2.5 |

TABLE 11-continued

| Sample | | % Added amount of εPL | Average particle diameter (μm) | % Water content | Difference of increase or loss | |
|---|---|---|---|---|---|---|
| | | | | | Not washed | Washed with flowing water for 30 min. |
| Example 40 | Poly-propylene Sheet-24 | 0.05 | 50 | 15.0 | 5.2 | 3.3 |
| Example 41 | Poly-propylene Sheet-25 | 0.05 | 200 | 15.0 | 4.0 | 3.0 |
| Example 42 | Poly-propylene Sheet-26 | 0.05 | 350 | 15.0 | 3.3 | 2.0 |
| Example 10 | Poly-propylene Sheet-1 | 1.0 | | 5.5 | 7.0 | 7.0 |
| Example 13 | Poly-propylene Sheet-5 | 0.5 | | 5.5 | 7.0 | 7.0 |
| Example 15 | Poly-propylene Sheet-8 | 0.1 | | 5.5 | 7.0 | 5.2 |
| Example 17 | Poly-propylene Sheet-11 | 0.05 | | 5.5 | 4.0 | 3.3 |
| Comparative Example 10 | Poly-propylene Sheet-14 | 0 | | Not added | 0 | 0 |

Name of bacteria: *Escherichia coli* (IFO3972)

As can be seen in Table 11, the specimens obtained in Examples 31 to 42 exert a sufficient antibacterial effect as compared with the specimens (free of εPL) obtained in Comparative Example 10. In particular, the specimens comprising an εPL having an average particle diameter of not more than 200 μm incorporated therein, despite its water content of 15.0% in εPL, exert the same antibacterial effect on *Escherichia coli* as the specimens (comprising an εPL having a water content of 5.5% incorporated therein) obtained in Examples 10, 13, 15 and 17, which exert an excellent antibacterial effect in Antibacterial effect test 3. In some detail, these specimens exert a high antibacterial effect on *Escherichia coli* as compared with the specimens (comprising an εPL having an average particle diameter of more than 200 μm incorporated therein) obtained in Examples 33, 36, 39 and 42 and fairly maintain its antibacterial effect even after washing with flowing water for 30 minutes.

content of 15.0% in εPL, exert the same antibacterial effect on *Staphylococcus aureus* as the specimens (comprising an εPL having a water content of 5.5% incorporated therein) obtained in Examples 10, 13, 15 and 17, which exert an excellent antibacterial effect in Antibacterial effect test 3. In some detail, these specimens exert a high antibacterial effect on *Staphylococcus aureus* as compared with the specimens (comprising an εPL having an average particle diameter of more than 200 μm incorporated therein) obtained in Examples 33, 36, 39 and 42 and fairly maintain its antibacterial effect even after washing with flowing water for 30 minutes.

<<Mixture of εPL and Surface Active Agent>>

(Preparation of Mixture of εPL and Surface Active Agent)

εPL-8

Into a 300 ml eggplant type flask were charged 50 ml of a 25% aqueous solution of εPL and 50 ml of a 25% aqueous

TABLE 12

| Sample | | % Added amount of εPL | Average particle diameter (μm) | % Water content | Difference of increase or loss | |
|---|---|---|---|---|---|---|
| | | | | | Not washed | Washed with flowing water for 30 min. |
| Example 31 | Poly-propylene Sheet-15 | 1.0 | 50 | 15.0 | 7.0 | 7.0 |
| Example 32 | Poly-propylene Sheet-16 | 1.0 | 200 | 15.0 | 7.0 | 7.0 |
| Example 33 | Poly-propylene Sheet-17 | 1.0 | 350 | 15.0 | 6.8 | 6.0 |
| Example 34 | Poly-propylene Sheet-18 | 0.5 | 50 | 15.0 | 7.0 | 7.0 |
| Example 35 | Poly-propylene Sheet-19 | 0.5 | 200 | 15.0 | 7.0 | 7.0 |
| Example 36 | Poly-propylene Sheet-20 | 0.5 | 350 | 15.0 | 5.5 | 4.0 |
| Example 37 | Poly-propylene Sheet-21 | 0.1 | 50 | 15.0 | 7.0 | 7.0 |
| Example 38 | Poly-propylene Sheet-22 | 0.1 | 200 | 15.0 | 7.0 | 5.5 |
| Example 39 | Poly-propylene Sheet-23 | 0.1 | 350 | 15.0 | 3.7 | 2.5 |
| Example 40 | Poly-propylene Sheet-24 | 0.05 | 50 | 15.0 | 5.2 | 3.5 |
| Example 41 | Poly-propylene Sheet-25 | 0.05 | 200 | 15.0 | 4.6 | 3.3 |
| Example 42 | Poly-propylene Sheet-26 | 0.05 | 350 | 15.0 | 3.5 | 2.2 |
| Example 10 | Poly-propylene Sheet-1 | 1.0 | | 5.5 | 7.0 | 7.0 |
| Example 13 | Poly-propylene Sheet-5 | 0.5 | | 5.5 | 7.0 | 7.0 |
| Example 15 | Poly-propylene Sheet-8 | 0.1 | | 5.5 | 6.8 | 4.3 |
| Example 17 | Poly-propylene Sheet-11 | 0.05 | | 5.5 | 4.0 | 3.2 |
| Comparative Example 10 | Poly-propylene Sheet-14 | 0 | | Not added | 0 | 0 |

Name of bacteria: *Staphylococcus aureus* (IFO12732)

As can be seen in Table 12, the specimens obtained in Examples 31 to 42 exert a sufficient antibacterial effect as compared with the specimens (free of εPL) obtained in Comparative Example 10. In particular, the specimens comprising an εPL having an average particle diameter of not more than 200 μm incorporated therein, despite its water solution of glycerin monostearate. The mixture was stirred thoroughly, frozen at a temperature of −40° C., and then freeze-dried in a vacuum freeze dryer for 48 hours to obtain εPL-8 as a mixture of the same proportion of εPL and glycerin monostearate.

εPL-9The procedure of εPL-8 was followed except that the surface active agent used was sorbitan ester monolaurate. As a result, εPL-9 was obtained as a mixture of the same proportion of εPL and sorbitan ester monolaurate.

εPL-10

The procedure of εPL-8 was followed except that the surface active agent used was $C_{12}$ alkyl glucoside. As a result, εPL-10 was obtained as a mixture of the same proportion of εPL and $C_{12}$ alkyl glucoside.

εPL-11

The procedure of εPL-8 was followed except that the surface active agent used was polyoxyethylene lauryl ether. As a result, εPL-11 was obtained as a mixture of the same proportion of εPL and polyoxyethylene lauryl ether.

εPL-12

The procedure of εPL-8 was followed except that the surface active agent used was lauryl dimethyl betaine. As a result, εPL-12 was obtained as a mixture of the same proportion of εPL and lauryl dimethyl betaine.

εPL-13

The procedure of εPL-8 was followed except that the surface active agent used was tallow trimethyl ammonium chloride. As a result, εPL-13 was obtained as a mixture of the same proportion of εPL and tallow trimethyl ammonium chloride.

The εPL incorporated in εPL-8 to εPL-13 had a water content of from 5 to 6% by weight.

EXAMPLE 43

The procedure of Example 1 was followed except that εPL-8 was added in an amount of 2.0% instead of εPL-1 in an amount of 1.0%. As a result, Polypropylene Sheet-27 was prepared.

EXAMPLE 44

The procedure of Example 1 was followed except that εPL-9 was added in an amount of 2.0% instead of εPL-1 in an amount of 1.0%. As a result, Polypropylene Sheet-28 was prepared.

EXAMPLE 45

The procedure of Example 1 was followed except that εPL-10 was added in an amount of 2.0% instead of εPL-1 in an amount of 1.0%. As a result, Polypropylene Sheet-29 was prepared.

EXAMPLE 46

The procedure of Example 1 was followed except that εPL-11 was added in an amount of 2.0% instead of εPL-1 in an amount of 1.0%. As a result, Polypropylene Sheet-30 was prepared.

EXAMPLE 47

The procedure of Example 1 was followed except that εPL-12 was added in an amount of 2.0% instead of εPL-1 in an amount of 1.0%. As a result, Polypropylene Sheet-31 was prepared.

EXAMPLE 48

The procedure of Example 1 was followed except that εPL-13 was added in an amount of 2.0% instead of εPL-1 in an amount of 1.0%. As a result, Polypropylene Sheet-32 was prepared.

(Test 5 for Observation of External Appearance of Sheet)

Polypropylene Sheet-1, 15 and 27 to 32 obtained in Examples 1, 19 and 43 to 48 were visually observed for external appearance. The results are shown in Table 13 below.

TABLE 13

| | Sample Name | Added amount of εPL (%) | Added amount of surface active agent (%) | External appearance of sheet by visual observation | Judgement |
|---|---|---|---|---|---|
| Example 43 | Polypropylene Sheet-27 | 1.0 | 1.0 | The dispersibility of εPL in the sheet and the smoothness of the sheet are extremely good. The sheet is acceptable in external appearance. | ⊚ |
| Example 44 | Polypropylene Sheet-28 | 1.0 | 1.0 | The dispersibility of εPL in the sheet and the smoothness of the sheet are extremely good The sheet is acceptable in external appearance. | ⊚ |
| Example 45 | Polypropylene Sheet-29 | 1.0 | 1.0 | The dispersibility of εPL in the sheet and the smoothness of the sheet are extremely good. The sheet is acceptable in external appearance. | ⊚ |
| Example 46 | Polypropylene Sheet-30 | 1.0 | 1.0 | The dispersibility of εPL in the sheet and the smoothness of the sheet are extremely good. The sheet is acceptable in external appearance. | ⊚ |
| Example 47 | Polypropylene Sheet-31 | 1.0 | 1.0 | The dispersibility of εPL in the sheet and the smoothness of the sheet are extremely good. The sheet is acceptable in external appearance. | ⊚ |
| Example 48 | Polypropylene Sheet-32 | 1.0 | 1.0 | The dispersibility of εPL in the sheet and the smoothness of the sheet are extremely good. The sheet is acceptable in external appearance. | ⊚ |
| Example 1 | Polypropylene Sheet-1 | 1.0 | 0 | The dispersibility of εPL in the sheet and the smoothness of the sheet are extremely good. The sheet is acceptable in external appearance. | ⊚ |
| Example 19 | Polypropylene Sheet-15 | 1.0 | 0 | The dispersibility of εPL in the sheet and the smoothness of the sheet are extremely good. The sheet is acceptable in external appearance. | ⊚ |

TABLE 13-continued

| Sample Name | Added amount of εPL (%) | Added amount of surface active agent (%) | External appearance of sheet by visual observation | Judgement |
|---|---|---|---|---|

⊚: Excellent external sheet appearance; judged applicable in wide application without any problem
○: Good external sheet appearance; judged applicable in many uses so far as high transparency and smoothness are not required
Δ: Slight poor external sheet appearance; judged difficultly applicable in uses requiring transparency and smoothness but applicable in uses requiring coloring
X: Poor external sheet appearance; judged inapplicable As can be seen in Table 13, the incorporation of εPL in admixture with a surface active agent makes it possible to enhance the dispersibility of εPL in the polypropylene sheet and provide the same external appearance and smoothness as that of the polypropylene sheet (comprising an εPL having a water content of 5.5% incorporated therein) obtained in Example 1 and the polypropylene sheet (comprising an εPL having an average particle diameter of 50 μm incorporated therein) obtained in Example 19.

EXAMPLE 49

The procedure of Example 1 was followed except that εPL-8 was added in an amount of 0.2% instead of εPL-1 in an amount of 1.0%. As a result, Polypropylene Sheet-33 was prepared.

EXAMPLE 50

The procedure of Example 1 was followed except that εPL-9 was added in an amount of 0.2% instead of εPL-1 in an amount of 1.0%. As a result, Polypropylene Sheet-34 was prepared.

EXAMPLE 51

The procedure of Example 1 was followed except that εPL-10 was added in an amount of 0.2% instead of εPL-1 in an amount of 1.0%. As a result, Polypropylene Sheet-35 was prepared.

EXAMPLE 52

The procedure of Example 1 was followed except that εPL-11 was added in an amount of 0.2% instead of εPL-1 in an amount of 1.0%. As a result, Polypropylene Sheet-36 was prepared.

EXAMPLE 53

The procedure of Example 1 was followed except that εPL-12 was added in an amount of 0.2% instead of εPL-1 in an amount of 1.0%. As a result, Polypropylene Sheet-37 was prepared.

EXAMPLE 54

The procedure of Example 1 was followed except that εPL-13 was added in an amount of 0.2% instead of εPL-1 in an amount of 1.0%. As a result, Polypropylene Sheet-38 was prepared.

Comparative Example 11

A 2.0% aqueous solution of εPL-8 was sprayed onto a polypropylene sheet prepared according to Comparative Example 5, and then dried in a 50° C. hot air dryer for 30 minutes to prepare Polypropylene Sheet-39 coated with a mixture of εPL and surface active agent.

Comparative Example 12

The procedure of Comparative Example 11 was followed except that a 2.0% aqueous solution of εPL-9 was used instead of the 2.0% aqueous solution of εPL-8. As a result, Polypropylene Sheet-40 was prepared.

Comparative Example 13

The procedure of Comparative Example 11 was followed except that a 2.0% aqueous solution of εPL-10 was used instead of the 2.0% aqueous solution of εPL-8. As a result, Polypropylene Sheet-41 was prepared.

Comparative Example 14

The procedure of Comparative Example 11 was followed except that a 2.0% aqueous solution of εPL-11 was used instead of the 2.0% aqueous solution of εPL-8. As a result, Polypropylene Sheet-42 was prepared.

Comparative Example 15

The procedure of Comparative Example 11 was followed except that a 2.0% aqueous solution of εPL-12 was used instead of the 2.0% aqueous solution of εPL-8. As a result, Polypropylene Sheet-43 was prepared.

Comparative Example 16

The procedure of Comparative Example 11 was followed except that a 2.0% aqueous solution of εPL-13 was used instead of the 2.0% aqueous solution of εPL-8. As a result, Polypropylene Sheet-44 was prepared.

Comparative Example 1

The procedure of Comparative Example 11 was followed except that a 1.0% aqueous solution of εPL was applied instead of the 2.0% aqueous solution of εPL-8. As a result, Polypropylene Sheet-45 was prepared.

(Antibacterial Effect Test 9)

Specimens (50×50×0.5 mm) prepared from Polypropylene Sheet-1, 6, 19, 25 and 43 to 54 obtained in Examples 1, 6, 19, 25 and 43 to 54 and Comparative Examples 5 and 11 to 17 were each washed with flowing tap water at a rate of 2 l/min for 0 to 60 minutes. The specimen thus washed was then subjected to antibacterial effect test 9 in the following manner.

Antibacterial Testing Method (SEK Shake Flask Method)

The antibacterial effect test 9 was conducted in accordance with SEK shake flask method defined in "Manual of test for evaluation of effect of antibacterial deodorized products", Association of Sanitary Processing of Textile Products. In some detail, into a screw-capped 100 ml conical flask was charged 29.7 ml of a phosphoric acid buffer having a pH value of 7.2. The flask was then capped. The material was sterilized by heat and moisture at 121° C. and 0.10 MPa in an autoclave for 15 minutes, and then allowed to cool to ordinary temperature. Subsequently, 0.3 ml of a bacterial liquid having *Escherichia coli* (IFO12734) suspended therein was incubated in the material through a sterilized pipette in such a manner that the viable cell count in the flask reached $3.5 \times 10^4$/ml. The above-described specimens were each dipped in the testing bacterial liquid. The flask was shaken at a testing temperature of 37° C. for 1 to 3 hours. The testing bacterial liquid thus treated was then measured for viable cell count by standard agar medium method. As a control there was used an untreated testing bacterial liquid. The control was subjected to blank test in the same manner as mentioned above. The measurements were then subjected to calculation for difference of increase or loss by the following equation. The results are shown in Tables 14 to 19 below.

Nonbactericidal Sample

[A]: Viable cell count shortly after incubation

[B]: Viable cell count after a predetermined time of shaking

Bactericidal Sample

[C]: Viable cell count after a predetermined time of shaking

Difference of increase or loss = $\log_{10}$ (B/A)–$\log_{10}$ (C/A)

TABLE 14

| | | Content | | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | Sample | Addition of εPL/ surface active agent mixture | εPL Concentration in mixture | 1 hr. | 3 hrs. | 1 hr. | 3 hrs. | 1 hr. | 3 hrs. |
| Example 43 | Polypropylene Sheet-27 | 2.0% added | 1.0% | 4.5 | 4.5 | 4.5 | 4.5 | 4.5 | 4.5 |
| Example 49 | Polypropylene Sheet-33 | 0.2% added | 0.1% | 2.2 | 4.5 | 4.5 | 4.5 | 0.8 | 4.5 |
| Example 1 | Polypropylene Sheet-1 | 0% added | 1.0% | 3.5 | 4.3 | 3.7 | 4.2 | 3.1 | 4.2 |
| Example 6 | Polypropylene Sheet-8 | 0% added | 0.1% | 2.5 | 4.5 | 2.3 | 4.4 | 1.6 | 3.5 |
| Example 19 | Polypropylene Sheet-15 | 0% added | 1.0% | 3.8 | 4.5 | 4.1 | 4.5 | 4.5 | 4.5 |
| Example 25 | Polypropylene Sheet-21 | 0% added | 0.1% | 2.5 | 4.5 | 3.5 | 4.1 | 1.6 | 2.8 |
| Comparative Example 5 | Polypropylene Sheet-14 | 0% added | 0% | 0 | 0 | 0 | 0 | 0 | 0 |
| Comparative Example 11 | Polypropylene Sheet-39 | 2.0% aqueous solution | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 15

| | | Content | | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | Sample | Addition of εPL/ surface active agent mixture | εPL Concentration in mixture | 1 hr. | 3 hrs. | 1 hr. | 3 hrs. | 1 hr. | 3 hrs. |
| Example 44 | Polypropylene Sheet-28 | 2.0% added | 1.0% | 4.5 | 4.5 | 4.5 | 4.5 | 4.5 | 4.5 |
| Example 50 | Polypropylene Sheet-34 | 0.2% added | 0.1% | 1.8 | 4.5 | 1.8 | 4.5 | 0.4 | 1.8 |
| Example 1 | Polypropylene Sheet-1 | 0% added | 1.0% | 3.5 | 4.3 | 3.7 | 4.2 | 3.1 | 4.2 |
| Example 6 | Polypropylene Sheet-8 | 0% added | 0.1% | 2.5 | 4.5 | 2.3 | 4.4 | 1.6 | 3.5 |
| Example 19 | Polypropylene Sheet-15 | 0% added | 1.0% | 3.8 | 4.5 | 4.1 | 4.5 | 4.5 | 4.5 |
| Example 25 | Polypropylene Sheet-21 | 0% added | 0.1% | 2.5 | 4.5 | 3.5 | 4.1 | 1.6 | 2.8 |
| Comparative Example 5 | Polypropylene Sheet-14 | 0% added | 0% | 0 | 0 | 0 | 0 | 0 | 0 |
| Comparative Example 12 | Polypropylene Sheet-40 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 16

| | Sample | Content Addition of εPL/ surface active agent mixture | εPL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 45 | Polypropylene Sheet-29 | 2.0% added | 1.0% | 4.5 | 4.5 | 1.8 | 4.5 | 1.8 | 4.5 |
| Example 51 | Polypropylene Sheet-35 | 0.2% added | 0.1% | 4.5 | 4.5 | 1.5 | 3.2 | 0.2 | 1.4 |
| Example 1 | Polypropylene Sheet-1 | 0% added | 1.0% | 3.5 | 4.3 | 3.7 | 4.2 | 3.1 | 4.2 |
| Example 6 | Polypropylene Sheet-8 | 0% added | 0.1% | 2.5 | 4.5 | 2.3 | 4.4 | 1.6 | 3.5 |
| Example 19 | Polypropylene Sheet-15 | 0% added | 1.0% | 3.8 | 4.5 | 4.1 | 4.5 | 4.5 | 4.5 |
| Example 25 | Polypropylene Sheet-21 | 0% added | 0.1% | 2.5 | 4.5 | 3.5 | 4.1 | 1.6 | 2.8 |
| Comparative Example 5 | Polypropylene Sheet-14 | 0% added | 0% | 0 | 0 | 0 | 0 | 0 | 0 |
| Comparative Example 13 | Polypropylene Sheet-41 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 17

| | Sample | Content Addition of εPL/ surface active agent mixture | εPL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 46 | Polypropylene Sheet-30 | 2.0% added | 1.0% | 4.5 | 4.5 | 2.2 | 4.5 | 1.8 | 4.5 |
| Example 52 | Polypropylene Sheet-36 | 0.2% added | 0.1% | 1.8 | 4.5 | 1.3 | 1.8 | 1.3 | 1.8 |
| Example 1 | Polypropylene Sheet-1 | 0% added | 1.0% | 3.5 | 4.3 | 3.7 | 4.2 | 3.1 | 4.2 |
| Example 6 | Polypropylene Sheet-8 | 0% added | 0.1% | 2.5 | 4.5 | 2.3 | 4.4 | 1.6 | 3.5 |
| Example 19 | Polypropylene Sheet-15 | 0% added | 1.0% | 3.8 | 4.5 | 4.1 | 4.5 | 4.5 | 4.5 |
| Example 25 | Polypropylene Sheet-21 | 0% added | 0.1% | 2.5 | 4.5 | 3.5 | 4.1 | 1.6 | 2.8 |
| Comparative Example 5 | Polypropylene Sheet-14 | 0% added | 0% | 0 | 0 | 0 | 0 | 0 | 0 |
| Comparative Example 14 | Polypropylene Sheet-42 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 18

| | | Content | | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | Sample | Addition of εPL/ surface active agent mixture | εPL Concen- tration in mixture | 1 hr. | 3 hrs. | 1 hr. | 3 hrs. | 1 hr. | 3 hrs. |
| Example 47 | Polypropylene Sheet-31 | 2.0% added | 1.0% | 4.5 | 4.5 | 4.5 | 4.5 | 4.5 | 4.5 |
| Example 53 | Polypropylene Sheet-37 | 0.2% added | 0.1% | 4.5 | 4.5 | 4.5 | 1.8 | 4.5 | 1.8 |
| Example 1 | Polypropylene Sheet-1 | 0% added | 1.0% | 3.5 | 4.3 | 3.7 | 4.2 | 3.1 | 4.2 |
| Example 6 | Polypropylene Sheet-8 | 0% added | 0.1% | 2.5 | 4.5 | 2.3 | 4.4 | 1.6 | 3.5 |
| Example 19 | Polypropylene Sheet-15 | 0% added | 1.0% | 3.8 | 4.5 | 4.1 | 4.5 | 4.5 | 4.5 |
| Example 25 | Polypropylene Sheet-21 | 0% added | 0.1% | 2.5 | 4.5 | 3.5 | 4.1 | 1.6 | 2.8 |
| Comparative Example 5 | Polypropylene Sheet-14 | 0% added | 0% | 0 | 0 | 0 | 0 | 0 | 0 |
| Comparative Example 15 | Polypropylene Sheet-43 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 19

| | | Content | | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | Sample | Addition of εPL/ surface active agent mixture | εPL Concen- tration in mixture | 1 hr. | 3 hrs. | 1 hr. | 3 hrs. | 1 hr. | 3 hrs. |
| Example 48 | Polypropylene Sheet-32 | 2.0% added | 1.0% | 4.5 | 4.5 | 4.5 | 4.5 | 4.5 | 4.5 |
| Example 54 | Polypropylene Sheet-38 | 0.2% added | 0.1% | 4.5 | 4.5 | 4.5 | 4.5 | 4.5 | 4.5 |
| Example 1 | Polypropylene Sheet-1 | 0% added | 1.0% | 3.5 | 4.3 | 3.7 | 4.2 | 3.1 | 4.2 |
| Example 6 | Polypropylene Sheet-8 | 0% added | 0.1% | 2.5 | 4.5 | 2.3 | 4.4 | 1.6 | 3.5 |
| Example 19 | Polypropylene Sheet-15 | 0% added | 1.0% | 3.8 | 4.5 | 4.1 | 4.5 | 4.5 | 4.5 |
| Example 25 | Polypropylene Sheet-21 | 0% added | 0.1% | 2.5 | 4.5 | 3.5 | 4.1 | 1.6 | 2.8 |
| Comparative Example 5 | Polypropylene Sheet-14 | 0% added | 0% | 0 | 0 | 0 | 0 | 0 | 0 |
| Comparative Example 16 | Polypropylene Sheet-44 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

As can be seen in Tables 14 to 19, the polypropylene sheets obtained in Examples 43 to 54 exert the same or higher antibacterial effect on *Escherichia coli* than the polypropylene sheets (comprising an εPL having a water content of 5.5% incorporated therein) obtained in Examples 1 and 6 and the polypropylene sheets (comprising an εPL having an average particle diameter of 50 μm incorporated therein) obtained in Examples 19 and 25. Further, these polypropylene sheets exert an excellent antibacterial effect after 30 to 60 minutes of washing as compared with those obtained in Comparative Examples 11 to 17, though showing the same antibacterial effect on unwashed specimen as the comparative examples.

(Antibacterial Effect Test 10)

Specimens (50×50×0.5 mm) prepared from Polypropylene Sheet-1, 8, 14, 15, 21 and 27 to 45 obtained in Examples 1, 6, 19, 25 and 43 to 54 and Comparative Examples 5 and 11 to 17 were each washed with flowing tap water at a rate of 2 l/min for 0 to 60 minutes. These specimens were each subjected to antibacterial effect test in the same manner as described in Test 9 except that as a testing bacteria there was used *Staphylococcus aureus* (IFO12732) instead of *Escherichia coli*. The results are shown in Tables 20 to 25 below.

TABLE 20

| | | Content | | Difference of increase or loss | | | | | |
| --- | --- | --- | --- | --- | --- | --- | --- | --- | --- |
| | | Addition of εPL/surface active agent | εPL Concentration in | Not washed Shaken | | Washed with flowing water for 30 min. Shaken | | Washed with flowing water for 60 min. Shaken | |
| | Sample | mixture | mixture | 1 hr. | 3 hrs. | 1 hr. | 3 hrs. | 1 hr. | 3 hrs. |
| Example 43 | Polypropylene Sheet-27 | 2.0% added | 1.0% | 4.5 | 4.5 | 4.5 | 4.5 | 4.5 | 4.5 |
| Example 49 | Polypropylene Sheet-33 | 0.2% added | 0.1% | 2.2 | 4.5 | 4.5 | 4.5 | 0.8 | 4.5 |
| Example 1 | Polypropylene Sheet-1 | 0% added | 1.0% | 4.2 | 4.0 | 4.1 | 4.5 | 4.1 | 4.5 |
| Example 6 | Polypropylene Sheet-8 | 0% added | 0.1% | 3.8 | 3.5 | 4.0 | 4.5 | 2.0 | 2.5 |
| Example 19 | Polypropylene Sheet-15 | 0% added | 1.0% | 4.5 | 4.5 | 4.5 | 4.5 | 4.5 | 4.5 |
| Example 23 | Polypropylene Sheet-21 | 0% added | 0.1% | 3.9 | 4.3 | 3.9 | 4.5 | 1.7 | 3.6 |
| Comparative Example 5 | Polypropylene Sheet-14 | 0% added | 0% | 0 | 0 | 0 | 0 | 0 | 0 |
| Comparative Example 11 | Polypropylene Sheet-39 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Staphylococcus aureus* (IFO12732)

TABLE 21

| | | Content | | Difference of increase or loss | | | | | |
| --- | --- | --- | --- | --- | --- | --- | --- | --- | --- |
| | | Addition of εPL/surface active agent | εPL Concentration in | Not washed Shaken | | Washed with flowing water for 30 min. Shaken | | Washed with flowing water for 60 min. Shaken | |
| | Sample | mixture | mixture | 1 hr. | 3 hrs. | 1 hr. | 3 hrs. | 1 hr. | 3 hrs. |
| Example 44 | Polypropylene Sheet-28 | 2.0% added | 1.0% | 4.5 | 4.5 | 4.5 | 4.5 | 4.5 | 4.5 |
| Example 50 | Polypropylene Sheet-34 | 0.2% added | 0.1% | 4.5 | 4.5 | 1.5 | 4.5 | 1.1 | 4.5 |
| Example 1 | Polypropylene Sheet-1 | 0% added | 1.0% | 4.2 | 4.0 | 4.1 | 4.5 | 4.1 | 4.5 |
| Example 6 | Polypropylene Sheet-8 | 0% added | 0.1% | 3.8 | 3.5 | 4.0 | 4.5 | 2.0 | 2.5 |
| Example 19 | Polypropylene Sheet-15 | 0% added | 1.0% | 4.5 | 4.5 | 4.5 | 4.5 | 4.5 | 4.5 |
| Example 25 | Polypropylene Sheet-21 | 0% added | 0.1% | 3.9 | 4.3 | 3.9 | 4.5 | 1.7 | 3.6 |
| Comparative Example 5 | Polypropylene Sheet-14 | 0% added | 0% | 0 | 0 | 0 | 0 | 0 | 0 |
| Comparative Example 12 | Polypropylene Sheet-40 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Staphylococcus aureus* (IFO12732)

TABLE 22

| | Sample | Content: Addition of εPL/surface active agent in mixture | Content: εPL Concentration in mixture | Difference of increase or loss |  |  |  |  |  |
|---|---|---|---|---|---|---|---|---|---|
| | | | | Not washed Shaken 1 hr. | Not washed Shaken 3 hrs. | Washed with flowing water for 30 min. Shaken 1 hr. | Washed with flowing water for 30 min. Shaken 3 hrs. | Washed with flowing water for 60 min. Shaken 1 hr. | Washed with flowing water for 60 min. Shaken 3 hrs. |
| Example 45 | Polypropylene Sheet-29 | 2.0% added | 1.0% | 4.5 | 4.5 | 4.5 | 4.5 | 4.5 | 4.5 |
| Example 51 | Polypropylene Sheet-35 | 0.2% added | 0.1% | 4.5 | 4.5 | 4.5 | 4.5 | 4.5 | 4.5 |
| Example 1 | Polypropylene Sheet-1 | 0% added | 1.0% | 4.2 | 4.0 | 4.1 | 4.5 | 4.1 | 4.5 |
| Example 6 | Polypropylene Sheet-8 | 0% added | 0.1% | 3.8 | 3.5 | 4.0 | 4.5 | 2.0 | 2.5 |
| Example 19 | Polypropylene Sheet-15 | 0% added | 1.0% | 4.5 | 4.5 | 4.5 | 4.5 | 4.5 | 4.5 |
| Example 25 | Polypropylene Sheet-21 | 0% added | 0.1% | 3.9 | 4.3 | 3.9 | 4.5 | 1.7 | 3.6 |
| Comparative Example 5 | Polypropylene Sheet-14 | 0% added | 0% | 0 | 0 | 0 | 0 | 0 | 0 |
| Comparative Example 13 | Polypropylene Sheet-41 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Staphylococcus aureus* (IFO12732)

TABLE 23

| | Sample | Content: Addition of εPL/surface active agent in mixture | Content: εPL Concentration in mixture | Difference of increase or loss |  |  |  |  |  |
|---|---|---|---|---|---|---|---|---|---|
| | | | | Not washed Shaken 1 hr. | Not washed Shaken 3 hrs. | Washed with flowing water for 30 min. Shaken 1 hr. | Washed with flowing water for 30 min. Shaken 3 hrs. | Washed with flowing water for 60 min. Shaken 1 hr. | Washed with flowing water for 60 min. Shaken 3 hrs. |
| Example 46 | Polypropylene Sheet-30 | 2.0% added | 1.0% | 4.5 | 4.5 | 1.8 | 4.5 | 3.0 | 4.5 |
| Example 52 | Polypropylene Sheet-36 | 0.2% added | 0.1% | 4.5 | 4.5 | 1.3 | 1.8 | 1.1 | 2.2 |
| Example 1 | Polypropylene Sheet-1 | 0% added | 1.0% | 4.2 | 4.0 | 4.1 | 4.5 | 4.1 | 4.5 |
| Example 6 | Polypropylene Sheet-8 | 0% added | 0.1% | 3.8 | 3.5 | 4.0 | 4.5 | 2.0 | 2.5 |
| Example 19 | Polypropylene Sheet-15 | 0% added | 1.0% | 4.5 | 4.5 | 4.5 | 4.5 | 4.5 | 4.5 |
| Example 25 | Polypropylene Sheet-21 | ' 0% added | 0.1% | 3.9 | 4.3 | 3.9 | 4.5 | 1.7 | 3.6 |
| Comparative Example 5 | Polypropylene Sheet-14 | 0% added | 0% | 0 | 0 | 0 | 0 | 0 | 0 |
| Comparative Example 14 | Polypropylene Sheet-42 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Staphylococcus aureus* (IFO12732)

TABLE 24

| | | Content | | Difference of increase or loss | | | | | |
| | | | | Not washed Shaken | | Washed with flowing water for 30 min. Shaken | | Washed with flowing water for 60 min. Shaken | |
| | Sample | Addition of εPL/surface active agent mixture | εPL Concentration in mixture | 1 hr. | 3 hrs. | 1 hr. | 3 hrs. | 1 hr. | 3 hrs. |
|---|---|---|---|---|---|---|---|---|---|
| Example 47 | Polypropylene Sheet-31 | 2.0% added | 1.0% | 4.5 | 4.5 | 4.5 | 4.5 | 4.5 | 4.5 |
| Example 53 | Polypropylene Sheet-37 | 0.2% added | 0.1% | 4.5 | 4.5 | 4.5 | 4.5 | 4.5 | 4.5 |
| Example 1 | Polypropylene Sheet-1 | 0% added | 1.0% | 4.2 | 4.0 | 4.1 | 4.5 | 4.1 | 4.5 |
| Example 6 | Polypropylene Sheet-8 | 0% added | 0.1% | 3.8 | 3.5 | 4.0 | 4.5 | 2.0 | 2.5 |
| Example 19 | Polypropylene Sheet-15 | 0% added | 1.0% | 4.5 | 4.5 | 4.5 | 4.5 | 4.5 | 4.5 |
| Example 25 | Polypropylene Sheet-21 | 0% added | 0.1% | 3.9 | 4.3 | 3.9 | 4.5 | 1.7 | 3.6 |
| Comparative Example 5 | Polypropylene Sheet-14 | 0% added | 0% | 0 | 0 | 0 | 0 | 0 | 0 |
| Comparative Example 15 | Polypropylene Sheet-43 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Staphylococcus aureus* (IFO12732)

TABLE 25

| | | Content | | Difference of increase or loss | | | | | |
| | | | | Not washed Shaken | | Washed with flowing water for 30 min. Shaken | | Washed with flowing water for 60 min. Shaken | |
| | Sample | Addition of εPL/surface active agent mixture | εPL Concentration in mixture | 1 hr. | 3 hrs. | 1 hr. | 3 hrs. | 1 hr. | 3 hrs. |
|---|---|---|---|---|---|---|---|---|---|
| Example 48 | Polypropylene Sheet-32 | 2.0% added | 1.0% | 4.5 | 4.5 | 4.5 | 4.5 | 4.5 | 4.5 |
| Example 54 | Polypropylene Sheet-38 | 0.2% added | 0.1% | 4.5 | 4.5 | 4.5 | 4.5 | 4.5 | 4.5 |
| Example 1 | Polypropylene Sheet-1 | 0% added | 1.0% | 4.2 | 4.0 | 4.1 | 4.5 | 4.1 | 4.5 |
| Example 6 | Polypropylene Sheet-8 | 0% added | 0.1% | 3.8 | 3.5 | 4.0 | 4.5 | 2.0 | 2.5 |
| Example 19 | Polypropylene Sheet-15 | 0% added | 1.0% | 4.5 | 4.5 | 4.5 | 4.5 | 4.5 | 4.5 |
| Example 25 | Polypropylene Sheet-21 | 0% added | 0.1% | 3.9 | 4.3 | 3.9 | 4.5 | 1.7 | 3.6 |
| Comparative Example 5 | Polypropylene Sheet-14 | 0% added | 0% | 0 | 0 | 0 | 0 | 0 | 0 |
| Comparative Example 16 | Polypropylene Sheet-44 | 2.0% aqueous solution sprayed | 1.0% | 4.5 | 4.5 | 0 | 0 | 0 | 0 |
| Comparative Example 17 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Staphylococcus aureus* (IFO12732)

As can be seen in Tables 20 to 25, the polypropylene sheets obtained in Examples 43 to 54 exert the same or higher antibacterial effect on *Staphylococcus aureus* than the polypropylene sheets (comprising an εPL having a water content of 5.5% incorporated therein) obtained in Examples 1 and 6 and the polypropylene sheets (comprising an εPL having an average particle diameter of 50 μm incorporated therein) obtained in Examples 19 and 25. Further, these polypropylene sheets exert an excellent antibacterial effect after 30 to 60 minutes of washing as compared with those obtained in Comparative Examples 11 to 17, though showing the same antibacterial effect on unwashed specimen as the comparative examples.

EXAMPLE 55

The procedure of Example 10 was followed except that εPL-8 was added in an amount of 2.0% instead of εPL-1 in an amount of 1.0%. As a result, Unsaturated Polyester Sheet-27 was prepared.

EXAMPLE 56

The procedure of Example 10 was followed except that εPL-9 was added in an amount of 2.0% instead of εPL-1 in an amount of 1.0%. As a result, Unsaturated Polyester Sheet-28 was prepared.

EXAMPLE 57

The procedure of Example 10 was followed except that εPL-10 was added in an amount of 2.0% instead of εPL-1 in an amount of 1.0%. As a result, Unsaturated Polyester Sheet-29 was prepared.

EXAMPLE 58

The procedure of Example 10 was followed except that εPL-11 was added in an amount of 2.0% instead of εPL-1 in an amount of 1.0%. As a result, Unsaturated Polyester Sheet-30 was prepared.

EXAMPLE 59

The procedure of Example 10 was followed except that εPL-12 was added in an amount of 2.0% instead of εPL-1 in an amount of 1.0%. As a result, Unsaturated Polyester Sheet-31 was prepared.

EXAMPLE 60

The procedure of Example 10 was followed except that εPL-13 was added in an amount of 2.0% instead of εPL-1 in an amount of 1.0%. As a result, Unsaturated Polyester Sheet-32 was prepared.

(Test 6 for Observation of External Appearance of Sheet)

Unsaturated Polyester Sheet-1, 15 and 27 to 32 obtained in Examples 10, 31 and 55 to 60 were visually observed for external appearance. The results are shown in Table 26 below.

an εPL having a water content of 5.5% incorporated therein) obtained in Example 10 and the unsaturated polyester sheet (comprising an εPL having an average particle diameter of 50 μm incorporated therein) obtained in Example 31.

EXAMPLE 61

The procedure of Example 1 was followed except that εPL-8 was added in an amount of 0.2% instead of εPL-1 in an amount of 1.0%. As a result, Unsaturated Polyester Sheet-33 was prepared.

EXAMPLE 62

The procedure of Example 1 was followed except that εPL-9 was added in an amount of 0.2% instead of εPL-1 in an amount of 1.0%. As a result, Unsaturated Polyester Sheet-34 was prepared.

EXAMPLE 63

The procedure of Example 1 was followed except that εPL-10 was added in an amount of 0.2% instead of εPL-1 in an amount of 1.0%. As a result, Unsaturated Polyester Sheet-35 was prepared.

EXAMPLE 64

The procedure of Example 1 was followed except that εPL-11 was added in an amount of 0.2% instead of εPL-1 in

TABLE 26

| Sample Name | | Added amount of εPL (%) | Added amount of surface active agent (%) | External appearance of sheet by visual observation | Judgement |
|---|---|---|---|---|---|
| Example 55 | Unsaturated Polyester Sheet-27 | 1.0 | 1.0 | The dispersibility of εPL in the sheet and the smoothness of the sheet are extremely good. The sheet is acceptable in external appearance. | ⊚ |
| Example 56 | Unsaturated Polyester Sheet-28 | 1.0 | 1.0 | The dispersibility of εPL in the sheet and the smoothness of the sheet are extremely good. The sheet is acceptable in external appearance. | ⊚ |
| Example 57 | Unsaturated Polyester Sheet-29 | 1.0 | 1.0 | The dispersibility of εPL in the sheet and the smoothness of the sheet are extremely good. The sheet is acceptable in external appearance. | ⊚ |
| Example 58 | Unsaturated Polyester Sheet-30 | 1.0 | 1.0 | The dispersibility of εPL in the sheet and the smoothness of the sheet are extremely good. The sheet is acceptable in external appearance. | ⊚ |
| Example 59 | Unsaturated Polyester Sheet-31 | 1.0 | 1.0 | The dispersibility of εPL in the sheet and the smoothness of the sheet are extremely good. The sheet is acceptable in external appearance. | ⊚ |
| Example 60 | Unsaturated Polyester Sheet-32 | 1.0 | 1.0 | The dispersibility of εPL in the sheet and the smoothness of the sheet are extremely good. The sheet is acceptable in external appearance. | ⊚ |
| Example 60 | Unsaturated Polyester Sheet-32 | 1.0 | 0 | The dispersibility of εPL in the sheet and the smoothness of the sheet are extremely good. The sheet is acceptable in external appearance. | ⊚ |
| Example 10 | Unsaturated Polyester Sheet-1 | 1.0 | 0 | The dispersibility of εPL in the sheet and the smoothness of the sheet are extremely good. The sheet is acceptable in external appearance. | ⊚ |
| Example 31 | Unsaturated Polyester Sheet-15 | 1.0 | 0 | The dispersibility of εPL in the sheet and the smoothness of the sheet are extremely good. The sheet is acceptable in external appearance. | ⊚ |

⊚: Excellent external sheet appearance; judged applicable in wide application without any problem
○: Good external sheet appearance; judged applicable in many uses so far as high transparency and smoothness are not required
Δ: Slight poor external sheet appearance; judged difficultly applicable in uses requiring transparency and smoothness but applicable in uses requiring coloring
X: Poor external sheet appearance; judged inapplicable As can be seen in Table 26, the incorporation of εPL in admixture with a surface active agent makes it possible to enhance the dispersibility of εPL in the unsaturated polyester sheet and provide the same external appearance and smoothness as that of the unsaturated polyester sheet (comprising an amount of 1.0%. As a result, Unsaturated Polyester Sheet-36 was prepared.

EXAMPLE 65

The procedure of Example 1 was followed except that εPL-12 was added in an amount of 0.2% instead of εPL-1 in an amount of 1.0%. As a result, Unsaturated Polyester Sheet-37 was prepared.

EXAMPLE 66

The procedure of Example 1 was followed except that εPL-13 was added in an amount of 0.2% instead of εPL-1 in an amount of 1.0%. As a result, Unsaturated Polyester Sheet-38 was prepared.

Comparative Example 18

A 2.0% aqueous solution of εPL-8 was sprayed onto a unsaturated polyester sheet prepared according to Comparative Example 5, and then dried in a 50° C. hot air dryer for 30 minutes to prepare Unsaturated Polyester Sheet-39 coated with a mixture of εPL and surface active agent.

Comparative Example 19

The procedure of Comparative Example 18 was followed except that a 2.0% aqueous solution of εPL-9 was used instead of the 2.0% aqueous solution of εPL-8. As a result, Unsaturated Polyester Sheet-40 was prepared.

Comparative Example 20

The procedure of Comparative Example 18 was followed except that a 2.0% aqueous solution of εPL-10 was used instead of the 2.0% aqueous solution of εPL-8. As a result, Unsaturated Polyester Sheet-41 was prepared.

Comparative Example 21

The procedure of Comparative Example 18 was followed except that a 2.0% aqueous solution of εPL-11 was used instead of the 2.0% aqueous solution of εPL-8. As a result, Unsaturated Polyester Sheet-42 was prepared.

Comparative Example 22

The procedure of Comparative Example 11 was followed except that a 2.0% aqueous solution of εPL-12 was used instead of the 2.0% aqueous solution of εPL-8. As a result, Unsaturated Polyester Sheet-43 was prepared.

Comparative Example 23

The procedure of Comparative Example 18 was followed except that a 2.0% aqueous solution of εPL-13 was used instead of the 2.0% aqueous solution of εPL-8. As a result, Unsaturated Polyester Sheet-44 was prepared.

Comparative Example 24

The procedure of Comparative Example 18 was followed except that a 1.0% aqueous solution of εPL was applied instead of the 2.0% aqueous solution of εPL-8. As a result, Unsaturated Polyester Sheet-45 was prepared.

Antibacterial Effect Test 11)

The procedure of antibacterial effect test 9 was followed except that Unsaturated Polyester Sheet-1, 8, 14, 15, 21 and 27 to 45 obtained in Examples 10, 15, 31, 37 and 55 to 66 and Comparative Examples 10 and 18 to 24 were used instead of Polypropylene Sheet-1, 8, 14, 15, 21 and 27 to 45. The results are shown in Tables 27 to 32 below.

TABLE 27

| | | Content | | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | Sample | Addition of εPL/surface active agent mixture | εPL Concentration in mixture | 1 hr. | 3 hrs. | 1 hr. | 3 hrs. | 1 hr. | 3 hrs. |
| Example 55 | Polypropylene Sheet-27 | 2.0% added | 1.0% | 4.5 | 4.5 | 4.5 | 4.5 | 4.5 | 4.5 |
| Example 61 | Polypropylene Sheet-33 | 0.2% added | 0.1% | 4.5 | 4.5 | 4.5 | 4.5 | 1.5 | 4.5 |
| Example 10 | Polypropylene Sheet-1 | 0% added | 1.0% | 4.5 | 4.5 | 4.5 | 4.5 | 4.5 | 4.5 |
| Example 15 | Polypropylene Sheet-8 | 0% added | 0.1% | 4.0 | 4.5 | 3.4 | 4.1 | 2.2 | 2.2 |
| Example 31 | Polypropylene Sheet-15 | 0% added | 1.0% | 4.5 | 4.5 | 4.3 | 4.5 | 4.0 | 4.5 |
| Example 37 | Polypropylene Sheet-21 | 0% added | 0.1% | 4.5 | 4.5 | 3.0 | 4.5 | 1.7 | 2.8 |
| Comparative Example 10 | Polypropylene Sheet-14 | 0% added | 0% | 0 | 0 | 0 | 0 | 0 | 0 |
| Comparative Example 18 | Polypropylene Sheet-39 | 2.0% aqueous solution sprayed | 1.0% | 4.5 | 4.5 | 0 | 0 | 0 | 0 |
| Comparative Example 24 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 28

| | | Content | | Difference of increase or loss | | | | | |
|---|---|---|---|---|---|---|---|---|---|
| | | Addition of ePL/surface active agent | ePL Concentration in | Not washed Shaken | | Washed with flowing water for 30 min. Shaken | | Washed with flowing water for 60 min. Shaken | |
| | Sample | mixture | mixture | 1 hr. | 3 hrs. | 1 hr. | 3 hrs. | 1 hr. | 3 hrs. |
| Example 56 | Polypropylene Sheet-28 | 2.0% added | 1.0% | 4.5 | 4.5 | 4.5 | 4.5 | 4.5 | 4.5 |
| Example 62 | Polypropylene Sheet-34 | 0.2% added | 0.1% | 3.4 | 4.5 | 2.8 | 4.5 | 1.4 | 3.0 |
| Example 10 | Polypropylene Sheet-1 | 0% added | 1.0% | 4.5 | 4.5 | 4.5 | 4.5 | 4.5 | 4.5 |
| Example 15 | Polypropylene Sheet-8 | 0% added | 0.1% | 4.0 | 4.5 | 3.4 | 4.1 | 2.2 | 2.2 |
| Example 31 | Polypropylene Sheet-15 | 0% added | 1.0% | 4.5 | 4.5 | 4.3 | 4.5 | 4.0 | 4.5 |
| Example 37 | Polypropylene Sheet-21 | 0% added | 0.1% | 4.5 | 4.5 | 3.0 | 4.5 | 1.7 | 2.8 |
| Comparative Example 10 | Polypropylene Sheet-14 | 0% added | 0% | 0 | 0 | 0 | 0 | 0 | 0 |
| Comparative Example 19 | Polypropylene Sheet-40 | 2.0% aqueous solution sprayed | 1.0% | 4.5 | 4.5 | 0 | 0 | 0 | 0 |
| Comparative Example 24 | Polypropylene Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 29

| | | Content | | Difference of increase or loss | | | | | |
|---|---|---|---|---|---|---|---|---|---|
| | | Addition of ePL/surface active agent | ePL Concentration in | Not washed Shaken | | Washed with flowing water for 30 min. Shaken | | Washed with flowing water for 60 min. Shaken | |
| | Sample | mixture | mixture | 1 hr. | 3 hrs. | 1 hr. | 3 hrs. | 1 hr. | 3 hrs. |
| Example 57 | Unsaturated Polyester Sheet-29 | 2.0% added | 1.0% | 4.5 | 4.5 | 2.0 | 4.5 | 2.5 | 4.5 |
| Example 63 | Unsaturated Polyester Sheet-35 | 0.2% added | 0.1% | 4.5 | 4.5 | 2.0 | 3.3 | 1.0 | 1.8 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 4.0 | 4.5 | 3.4 | 4.1 | 2.2 | 2.2 |
| Example 31 | Unsaturated Polyester Sheet-15 | 0% added | 1.0% | 4.5 | 4.5 | 4.3 | 4.5 | 4.0 | 4.5 |
| Example 37 | Unsaturated Polyester Sheet-21 | 0% added | 0.1% | 4.5 | 4.5 | 3.0 | 4.5 | 1.7 | 2.8 |
| Comparative Example 10 | Unsaturated Polyester Sheet-14 | 0% added | 0% | 0 | 0 | 0 | 0 | 0 | 0 |
| Comparative Example 20 | Unsaturated Polyester Sheet-41 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 30

| | Sample | Content: Addition of εPL/surface active agent mixture | Content: εPL Concentration in mixture | Not washed Shaken 1 hr. | Not washed Shaken 3 hrs. | Washed with flowing water for 30 min. Shaken 1 hr. | Washed with flowing water for 30 min. Shaken 3 hrs. | Washed with flowing water for 60 min. Shaken 1 hr. | Washed with flowing water for 60 min. Shaken 3 hrs. |
|---|---|---|---|---|---|---|---|---|---|
| Example 58 | Unsaturated Polyester Sheet-30 | 2.0% added | 1.0% | 4.5 | 4.5 | 2.7 | 4.5 | 2.2 | 4.5 |
| Example 57 | Unsaturated Polyester Sheet-36 | 0.2% added | 0.1% | 4.5 | 4.5 | 2.5 | 3.5 | 2.2 | 2.3 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 4.0 | 4.5 | 3.4 | 4.1 | 2.2 | 2.2 |
| Example 31 | Unsaturated Polyester Sheet-15 | 0% added | 1.0% | 4.5 | 4.5 | 4.3 | 4.5 | 4.0 | 4.5 |
| Example 37 | Unsaturated Polyester Sheet-21 | 0% added | 0.1% | 4.5 | 4.5 | 3.0 | 4.5 | 1.7 | 2.8 |
| Comparative Example 10 | Unsaturated Polyester Sheet-14 | 0% added | 0% | 0 | 0 | 0 | 0 | 0 | 0 |
| Comparative Example 21 | Unsaturated Polyester Sheet-42 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 31

| | Sample | Content: Addition of εPL/surface active agent mixture | Content: εPL Concentration in mixture | Not washed Shaken 1 hr. | Not washed Shaken 3 hrs. | Washed with flowing water for 30 min. Shaken 1 hr. | Washed with flowing water for 30 min. Shaken 3 hrs. | Washed with flowing water for 60 min. Shaken 1 hr. | Washed with flowing water for 60 min. Shaken 3 hrs. |
|---|---|---|---|---|---|---|---|---|---|
| Example 59 | Unsaturated Polyester Sheet-31 | 2.0% added | 1.0% | 4.5 | 4.5 | 4.5 | 4.5 | 4.5 | 4.5 |
| Example 65 | Unsaturated Polyester Sheet-37 | 0.2% added | 0.1% | 4.5 | 4.5 | 4.0 | 4.5 | 2.8 | 3.0 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 4.0 | 4.5 | 3.4 | 4.1 | 2.2 | 2.2 |
| Example 31 | Unsaturated Polyester Sheet-15 | 0% added | 1.0% | 4.5 | 4.5 | 4.3 | 4.5 | 4.0 | 4.5 |
| Example 37 | Unsaturated Polyester Sheet-21 | 0% added | 0.1% | 4.5 | 4.5 | 3.0 | 4.5 | 1.7 | 2.8 |
| Comparative Example 10 | Unsaturated Polyester Sheet-14 | 0% added | 0% | 0 | 0 | 0 | 0 | 0 | 0 |
| Comparative Example 22 | Unsaturated Polyester Sheet-43 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 32

| | Sample | Content Addition of ePL/surface active agent mixture | ePL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 60 | Unsaturated Polyester Sheet-32 | 2.0% added | 1.0% | 4.5 | 4.5 | 4.5 | 4.5 | 4.5 | 4.5 |
| Example 66 | Unsaturated Polyester Sheet-38 | 0.2% added | 0.1% | 4.5 | 4.5 | 4.5 | 4.5 | 3.5 | 4.5 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 4.0 | 4.5 | 3.4 | 4.1 | 2.2 | 2.2 |
| Example 31 | Unsaturated Polyester Sheet-15 | 0% added | 1.0% | 4.5 | 4.5 | 4.3 | 4.5 | 4.0 | 4.5 |
| Example 37 | Unsaturated Polyester Sheet-21 | 0% added | 0.1% | 4.5 | 4.5 | 3.0 | 4.5 | 1.7 | 2.8 |
| Comparative Example 10 | Unsaturated Polyester Sheet-14 | 0% added | 0% | 0 | 0 | 0 | 0 | 0 | 0 |
| Comparative Example 23 | Unsaturated Polyester Sheet-44 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

As can be seen in Tables 27 to 32, the unsaturated polyester sheets obtained in Examples 55 to 66 exert the same or higher antibacterial effect on *Escherichia coli* than the unsaturated polyester sheets (comprising an ePL having a water content of 5.5% incorporated therein) obtained in Examples 10 and 15 and the unsaturated polyester sheets (comprising an ePL having an average particle diameter of 50 μm incorporated therein) obtained in Examples 31 and 37. Further, these unsaturated polyester sheets exert an excellent antibacterial effect after 30 to 60 minutes of washing as compared with those obtained in Comparative Examples 18 to 24, though showing the same antibacterial effect on unwashed specimen as the comparative examples.

(Antibacterial Effect Test 12)

The procedure of antibacterial effect test 10 was followed except that Unsaturated Polyester Sheet-1, 8, 14, 15, 21 and 27 to 45 obtained in Examples 10, 15, 31, 37 and 55 to 66 and Comparative Examples 10 and 18 to 24 were used instead of Polypropylene Sheet-1, 8, 14, 15, 21 and 27 to 45. The results are shown in Tables 33 to 38 below.

TABLE 33

| | Sample | Content Addition of ePL/surface active agent mixture | ePL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 55 | Unsaturated Polyester Sheet-27 | 2.0% added | 1.0% | 4.5 | 4.5 | 4.5 | 4.5 | 4.5 | 4.5 |
| Example 61 | Unsaturated Polyester Sheet-33 | 0.2% added | 0.1% | 4.5 | 4.5 | 4.5 | 4.5 | 1.3 | 4.5 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 3.3 | 4.5 | 4.0 | 4.5 | 2.3 | 2.8 |
| Example 31 | Unsaturated Polyester Sheet-15 | 0% added | 1.0% | 4.5 | 4.5 | 4.1 | 4.5 | 4.1 | 4.5 |
| Example 37 | Unsaturated Polyester Sheet-21 | 0% added | 0.1% | 2.9 | 4.5 | 3.5 | 4.5 | 1.5 | 2.8 |
| Comparative Example 10 | Unsaturated Polyester Sheet-14 | 0% added | 0% | 0 | 0 | 0 | 0 | 0 | 0 |
| Comparative Example 18 | Unsaturated Polyester Sheet-39 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 34

| | Sample | Content: Addition of εPL/surface active agent mixture | Content: εPL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 56 | Unsaturated Polyester Sheet-28 | 2.0% added | 1.0% | 4.5 | 4.5 | 4.5 | 4.5 | 4.5 | 4.5 |
| Example 62 | Unsaturated Polyester Sheet-34 | 0.2% added | 0.1% | 4.5 | 4.5 | 3.6 | 4.5 | 2.2 | 4.5 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 3.3 | 4.5 | 4.0 | 4.5 | 2.3 | 2.8 |
| Example 31 | Unsaturated Polyester Sheet-15 | 0% added | 1.0% | 4.5 | 4.5 | 4.1 | 4.5 | 4.1 | 4.5 |
| Example 37 | Unsaturated Polyester Sheet-21 | 0% added | 0.1% | 2.9 | 4.5 | 3.5 | 4.5 | 1.5 | 2.8 |
| Comparative Example 10 | Unsaturated Polyester Sheet-14 | 0% added | 0% | 0 | 0 | 0 | 0 | 0 | 0 |
| Comparative Example 19 | Unsaturated Polyester Sheet-40 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 35

| | Sample | Content: Addition of εPL/surface active agent mixture | Content: εPL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 57 | Unsaturated Polyester Sheet-29 | 2.0% added | 1.0% | 4.5 | 4.5 | 4.5 | 4.5 | 4.5 | 4.5 |
| Example 63 | Unsaturated Polyester Sheet-35 | 0.2% added | 0.1% | 4.5 | 4.5 | 4.5 | 4.5 | 4.5 | 4.5 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 3.3 | 4.5 | 4.0 | 4.5 | 2.3 | 2.8 |
| Example 31 | Unsaturated Polyester Sheet-15 | 0% added | 1.0% | 4.5 | 4.5 | 4.1 | 4.5 | 4.1 | 4.5 |
| Example 37 | Unsaturated Polyester Sheet-21 | 0% added | 0.1% | 2.9 | 4.5 | 3.5 | 4.5 | 1.5 | 2.8 |
| Comparative Example 10 | Unsaturated Polyester Sheet-14 | 0% added | 0% | 0 | 0 | 0 | 0 | 0 | 0 |
| Comparative Example 20 | Unsaturated Polyester Sheet-41 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 36

| | Sample | Content: Addition of εPL/surface active agent mixture | Content: εPL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 58 | Unsaturated Polyester Sheet-30 | 2.0% added | 1.0% | 4.5 | 4.5 | 4.5 | 4.5 | 3.0 | 4.5 |
| Example 57 | Unsaturated Polyester Sheet-36 | 0.2% added | 0.1% | 4.5 | 4.5 | 1.9 | 1.9 | 1.2 | 2.5 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 3.3 | 4.5 | 4.0 | 4.5 | 2.3 | 2.8 |
| Example 31 | Unsaturated Polyester Sheet-15 | 0% added | 1.0% | 4.5 | 4.5 | 4.1 | 4.5 | 4.1 | 4.5 |
| Example 37 | Unsaturated Polyester Sheet-21 | 0% added | 0.1% | 2.9 | 4.5 | 3.5 | 4.5 | 1.5 | 2.8 |
| Comparative Example 10 | Unsaturated Polyester Sheet-14 | 0% added | 0% | 0 | 0 | 0 | 0 | 0 | 0 |
| Comparative Example 21 | Unsaturated Polyester Sheet-42 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 37

| | Sample | Content: Addition of εPL/surface active agent mixture | Content: εPL Concentration in mixture | Difference of increase or loss | | | | | |
|---|---|---|---|---|---|---|---|---|---|
| | | | | Not washed Shaken | | Washed with flowing water for 30 min. Shaken | | Washed with flowing water for 60 min. Shaken | |
| | | | | 1 hr. | 3 hrs. | 1 hr. | 3 hrs. | 1 hr. | 3 hrs. |
| Example 59 | Unsaturated Polyester Sheet-31 | 2.0% added | 1.0% | 4.5 | 4.5 | 4.5 | 4.5 | 4.5 | 4.5 |
| Example 65 | Unsaturated Polyester Sheet-37 | 0.2% added | 0.1% | 4.5 | 4.5 | 4.5 | 4.5 | 4.5 | 4.5 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 3.3 | 4.5 | 4.0 | 4.5 | 2.3 | 2.8 |
| Example 31 | Unsaturated Polyester Sheet-15 | 0% added | 1.0% | 4.5 | 4.5 | 4.1 | 4.5 | 4.1 | 4.5 |
| Example 37 | Unsaturated Polyester Sheet-21 | 0% added | 0.1% | 2.9 | 4.5 | 3.5 | 4.5 | 1.5 | 2.8 |
| Comparative Example 10 | Unsaturated Polyester Sheet-14 | 0% added | 0% | 0 | 0 | 0 | 0 | 0 | 0 |
| Comparative Example 22 | Unsaturated Polyester Sheet-43 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
| | Blank test | | | 0 | 0 | 0 | 0 | 0 | 0 |

Name of bacteria: *Escherichia coli* (IFO12734)

TABLE 38

|  |  | Content | | Difference of increase or loss | | | | | |
|---|---|---|---|---|---|---|---|---|---|
|  |  | Addition of εPL/surface active agent | εPL Concentration in | Not washed Shaken | | Washed with flowing water for 30 min. Shaken | | Washed with flowing water for 60 min. Shaken | |
|  | Sample | mixture | mixture | 1 hr. | 3 hrs. | 1 hr. | 3 hrs. | 1 hr. | 3 hrs. |
| Example 60 | Unsaturated Polyester Sheet-32 | 2.0% added | 1.0% | 4.5 | 4.5 | 4.5 | 4.5 | 4.5 | 4.5 |
| Example 66 | Unsaturated Polyester Sheet-38 | 0.2% added | 0.1% | 4.5 | 4.5 | 4.5 | 4.5 | 4.5 | 4.5 |
| Example 10 | Unsaturated Polyester Sheet-1 | 0% added | 1.0% | 4.5 | 4.5 | 4.5 | 4.5 | 4.5 | 4.5 |
| Example 15 | Unsaturated Polyester Sheet-8 | 0% added | 0.1% | 3.3 | 4.5 | 4.0 | 4.5 | 2.3 | 2.8 |
| Example 31 | Unsaturated Polyester Sheet-15 | 0% added | 1.0% | 4.5 | 4.5 | 4.1 | 4.5 | 4.1 | 4.5 |
| Example 37 | Unsaturated Polyester Sheet-21 | 0% added | 0.1% | 2.9 | 4.5 | 3.5 | 4.5 | 1.5 | 2.8 |
| Comparative Example 10 | Unsaturated Polyester Sheet-14 | 0% added | 0% | 0 | 0 | 0 | 0 | 0 | 0 |
| Comparative Example 23 | Unsaturated Polyester Sheet-44 | 2.0% aqueous solution sprayed | 1.0% | 4.5 | 4.5 | 0 | 0 | 0 | 0 |
| Comparative Example 24 | Unsaturated Polyester Sheet-45 | 1.0% aqueous solution sprayed | 1.0% | 4.5 | 4.5 | 0 | 0 | 0 | 0 |
|  | Blank test |  |  | 0 | 0 | 0 | 0 | 0 | 0 |

Name of bacteria: *Escherichia coli* (IFO12734)

As can be seen in Tables 33 to 38, the unsaturated polyester sheets obtained in Examples 55 to 66 exert the same or higher antibacterial effect on *Staphylococcus aureus* than the unsaturated polyester sheets (comprising an εPL having a water content of 5.5% incorporated therein) obtained in Examples 10 and 15 and the unsaturated polyester sheets (comprising an εPL having an average particle diameter of 50 μm incorporated therein) obtained in Examples 31 and 37. Further, these unsaturated polyester sheets exert an excellent antibacterial effect after 30 to 60 minutes of washing as compared with those obtained in Comparative Examples 18 to 24, though showing the same antibacterial effect on unwashed specimen as the comparative examples.

<<Combined Use of εPL/dispersant>>

EXAMPLE 67

A polypropylene (MFR: 10 g/10 min, 230° C., 21.18N), εPL-3 and zinc stearate as a dispersant were uniformly mixed in a blender in such a manner that the amount of the polypropylene, εPL-3 and zinc stearate were 99.6%, 0.1% and 0.3%, respectively. The mixture thus obtained was then packed into a mold having a size of 50 mm×50 mm×0.5 mm. The mold was then heat-compressed under a pressure of 19.61 MPa in a heat press which had been adjusted to 200° C. for 1 minute to prepare Polypropylene Sheet-46.

EXAMPLE 68

The procedure of Example 67 was followed except that the dispersant was changed to a polyethylene wax (Sanwax 131P, produced by SANYO CHEMICAL INDUSTRIES, LTD.). As a result, Polypropylene Sheet-47 was prepared.

EXAMPLE 69

The procedure of Example 67 was followed except that the dispersant was changed to amide stearate. As a result, Polypropylene Sheet-48 was prepared.

EXAMPLE 70

The procedure of Example 67 was followed except that the dispersant was changed to dioctyl phthalate. As a result, Polypropylene Sheet-49 was prepared.

EXAMPLE 71

The procedure of Example 67 was followed except that the dispersant was changed to i-octanol. As a result, Polypropylene Sheet-50 was prepared.

(Test 7 for Observation of External Appearance of Sheet)

Polypropylene Sheet-8, 22 and 46 to 50 obtained in Examples 6, 26 and 67 to 71 were visually observed for external appearance. The results are shown in Table 39 below.

TABLE 39

|  | Sample Name | Added amount of εPL (%) | Added amount of surface active agent (%) | External appearance of sheet by visual observation | Judgement |
|---|---|---|---|---|---|
| Example 67 | Polypropylene Sheet-46 | 0.1 | 0.3 | The dispersibility of εPL in the sheet and the smoothness of the sheet are extremely good. The sheet is acceptable in external appearance. | ⊚ |
| Example 68 | Polypropylene Sheet-47 | 0.1 | 0.3 | The dispersibility of εPL in the sheet and the smoothness of the sheet are extremely good. The sheet is acceptable in external appearance. | ⊚ |
| Example 69 | Polypropylene Sheet-48 | 0.1 | 0.3 | The dispersibility of εPL in the sheet and the smoothness of the sheet are extremely good. The sheet is acceptable in external appearance. | ⊚ |

TABLE 39-continued

| Sample Name | | Added amount of ∊PL (%) | Added amount of surface active agent (%) | External appearance of sheet by visual observation | Judgement |
|---|---|---|---|---|---|
| Example 70 | Polypropylene Sheet-49 | 0.1 | 0.3 | The dispersibility of ∊PL in the sheet and the smoothness of the sheet are extremely good. The sheet is acceptable in external appearance. | ⊙ |
| Example 71 | Polypropylene Sheet-50 | 0.1 | 0.3 | The dispersibility of ∊PL in the sheet and the smoothness of the sheet are extremely good. The sheet is acceptable in external appearance. | |
| Example 6 | Polypropylene Sheet-8 | 0.1 | 0 | The dispersibility of ∊PL in the sheet and the smoothness of the sheet are extremely good. The sheet is acceptable in external appearance | ⊙ |
| Example 26 | Polypropylene Sheet-22 | 0.1 | 0 | The dispersibility of ∊PL in the sheet and the smoothness of the sheet are extremely good. The sheet is acceptable in external appearance. | ⊙ |

⊙ : Excellent external sheet appearance; judged applicable in wide application without any problem
○ : Good external sheet appearance; judged applicable in many uses so far as high transparency and smoothness are not required
Δ: Slight poor external sheet appearance; judged difficultly applicable in uses requiring transparency and smoothness but applicable in uses requiring coloring
×: Poor external sheet appearance; judged inapplicable As can be seen in Table 39, the incorporation of ∊PL in combination with the dispersant makes it possible to enhance the dispersibility of ∊PL in the polypropylene sheet and provide the same external appearance and smoothness as that of the polypropylene sheet (comprising an ∊PL having a water content of 5.5% incorporated therein) obtained in Example 6 and the polypropylene sheet (comprising an ∊PL having an average particle diameter of 50 μm incorporated therein) obtained in Example 24.

EXAMPLE 72

The procedure of Example 67 was followed except that ∊PL-3 was added in an amount of 0.05% instead of 0.1%. As a result, Polypropylene Sheet-51 was prepared.

EXAMPLE 73

The procedure of Example 68 was followed except that ∊PL-3 was added in an amount of 0.05% instead of 0.1%. As a result, Polypropylene Sheet-52 was prepared.

EXAMPLE 74

The procedure of Example 69 was followed except that ∊PL-3 was added in an amount of 0.05% instead of 0.1%. As a result, Polypropylene Sheet-53 was prepared.

EXAMPLE -75

The procedure of Example 70 was followed except that ∊PL-3 was added in an amount of 0.05% instead of 0.1%. As a result, Polypropylene Sheet-54 was prepared.

EXAMPLE 76

The procedure of Example 71 was followed except that ∊PL-3 was added in an amount of 0.05% instead of 0.1%. As a result, Polypropylene Sheet-55 was prepared.

EXAMPLE 77

The procedure of Example 67 was followed except that ∊PL-3 was added in an amount of 0.5% instead of 0.1%. As a result, Polypropylene Sheet-56 was prepared.

EXAMPLE 78

The procedure of Example 68 was followed except that ∊PL-3 was added in an amount of 0.5% instead of 0.1%. As a result, Polypropylene Sheet-57 was prepared.

EXAMPLE 79

The procedure of Example 69 was followed except that ∊PL-3 was added in an amount of 0.5% instead of 0.1%. As a result, Polypropylene Sheet-58 was prepared.

EXAMPLE 80

The procedure of Example 70 was followed except that ∊PL-3 was added in an amount of 0.5% instead of 0.1%. As a result, Polypropylene Sheet-58 was prepared.

EXAMPLE 81

The procedure of Example 71 was followed except that ∊PL-3 was added in an amount of 0.5% instead of 0.1%. As a result, Polypropylene Sheet-60 was prepared.

(Antibacterial Effect Test 13)

The procedure of antibacterial effect test 1 was followed except that Polypropylene Sheet-5, 8, 11, 14, 18, 21, 24 and 46 to 60 obtained in Examples 4, 6, 8, 22, 25, 28 and 67 to 81 and Comparative Example 5 were used instead of Polypropylene Sheet-1 and 3 to 14. The results are shown in Table 40 below.

TABLE 40

| Sample Name | Polypropylene Sheet No. | % Added amount of εPL | Dispersant Name of dispersant | % Added amount | Difference of increase or loss Not washed | Washed with flowing water for 30 min. |
|---|---|---|---|---|---|---|
| Example 77 | 56 | 0.5 | Zinc stearate | 0.3 | 7.5 | 7.5 |
| Example 67 | 46 | 0.1 | Zinc stearate | 0.3 | 7.5 | 7.5 |
| Example 72 | 51 | 0.05 | Zinc stearate | 0.3 | 7.5 | 7.5 |
| Example 78 | 57 | 0.5 | Polyethlene wax | 0.3 | 7.5 | 7.5 |
| Example 68 | 47 | 0.1 | Polyethlene wax | 0.3 | 7.5 | 7.5 |
| Example 73 | 52 | 0.05 | Polyethlene wax | 0.3 | 7.5 | 5.5 |
| Example 79 | 58 | 0.5 | Amide stearate | 0.3 | 7.5 | 7.5 |
| Example 69 | 48 | 0.1 | Amide stearate | 0.3 | 7.5 | 7.5 |
| Example 74 | 53 | 0.05 | Amide stearate | 0.3 | 7.0 | 5.5 |
| Example 80 | 59 | 0.5 | Dioctyl phthalate | 0.3 | 7.5 | 7.5 |
| Example 70 | 49 | 0.1 | Dioctyl phthalate | 0.3 | 7.5 | 6.0 |
| Example 75 | 54 | 0.05 | Dioctyl phthalate | 0.3 | 7.5 | 5.0 |
| Example 81 | 60 | 0.5 | 1-Octanol | 0.3 | 7.5 | 7.5 |
| Example 71 | 50 | 0.1 | 1-Octanol | 0.3 | 7.0 | 5.7 |
| Example 76 | 55 | 0.05 | 1-Octanol | 0.3 | 7.0 | 5.2 |
| Example 4 | 5 | 0.5 | None | 0 | 7.0 | 7.0 |
| Example 6 | 8 | 0.1 | None | 0 | 7.0 | 5.2 |
| Example 8 | 11 | 0.05 | None | 0 | 4.0 | 3.3 |
| Example 22 | 18 | 0.5 | None | 0 | 7.0 | 7.0 |
| Example 25 | 21 | 0.1 | None | 0 | 7.0 | 7.0 |
| Example 28 | 24 | 0.05 | None | 0 | 5.2 | 3.3 |
| Comparative Example 5 | 14 | 0 | None | 0 | 0 | 0 |

Name of bacterial: *Escherichia coli* (IFO3972)

As can be seen in Table 40, the specimens obtained in Examples 67 to 81, despite its water content of 15.0% in εPL, exert the same or higher antibacterial effect on *Escherichia coli* than the specimens (comprising an εPL having a water content of 5.5% incorporated therein) obtained in Examples 4, 6 and 8 and the specimens (comprising an εPL having an average particle diameter of not more than 50 μm incorporated therein) obtained in Examples 22, 25 and 28.

(Antibacterial Effect Test 14)

The procedure of antibacterial effect test 2 was followed except that Polypropylene Sheet-5, 8, 11, 14, 18, 21, 24 and 46 to 60 obtained in Examples 4, 6, 8, 22, 25, 28 and 67 to 81 and Comparative Example 5 were used instead of Polypropylene Sheet-1 and 3 to 14. The results are shown in Table 41 below.

TABLE 41

| Sample Name | Polypropylene Sheet No. | % Added amount of εPL | Dispersant Name of dispersant | % Added amount | Difference of increase or loss Not washed | Washed with flowing water for 30 min. |
|---|---|---|---|---|---|---|
| Example 77 | 56 | 0.5 | Zinc stearate | 0.3 | 7.5 | 7.5 |
| Example 67 | 46 | 0.1 | Zinc stearate | 0.3 | 7.5 | 7.5 |
| Example 72 | 51 | 0.05 | Zinc stearate | 0.3 | 7.5 | 7.5 |
| Example 78 | 57 | 0.5 | Polyethlene wax | 0.3 | 7.5 | 7.5 |
| Example 68 | 47 | 0.1 | Polyethlene wax | 0.3 | 7.5 | 7.5 |
| Example 73 | 52 | 0.05 | Polyethlene wax | 0.3 | 7.0 | 6.0 |
| Example 79 | 58 | 0.5 | Amide stearate | 0.3 | 7.5 | 7.5 |
| Example 69 | 48 | 0.1 | Amide stearate | 0.3 | 7.5 | 7.5 |
| Example 74 | 53 | 0.05 | Amide stearate | 0.3 | 7.0 | 5.5 |
| Example 80 | 59 | 0.5 | Dioctyl phthalate | 0.3 | 7.5 | 7.5 |
| Example 70 | 49 | 0.1 | Dioctyl phthalate | 0.3 | 7.5 | 6.8 |
| Example 75 | 54 | 0.05 | Dioctyl phthalate | 0.3 | 6.6 | 5.5 |
| Example 81 | 60 | 0.5 | 1-Octanol | 0.3 | 7.5 | 7.5 |
| Example 71 | 50 | 0.1 | 1-Octanol | 0.3 | 7.0 | 6.5 |
| Example 76 | 55 | 0.05 | 1-Octanol | 0.3 | 7.1 | 5.0 |
| Example 4 | 5 | 0.5 | None | 0 | 7.0 | 7.0 |
| Example 6 | 8 | 0.1 | None | 0 | 6.8 | 4.3 |
| Example 8 | 11 | 0.05 | None | 0 | 4.0 | 3.2 |
| Example 22 | 18 | 0.5 | None | 0 | 7.0 | 7.0 |
| Example 25 | 21 | 0.1 | None | 0 | 7.0 | 7.0 |
| Example 28 | 24 | 0.05 | None | 0 | 5.2 | 3.5 |
| Comparative Example 5 | 14 | 0 | None | 0 | 0 | 0 |

Name of bacterial: *Staphylococcus aureus* (IFO12732)

As can be seen in Table 41, the specimens obtained in Examples 67 to 81, despite its water content of 15.0% in εPL, exert the same or higher antibacterial effect on *Staphylococcus aureus* than the specimens (comprising an εPL having a water content of 5.5% incorporated therein) obtained in Examples 4, 6 and 8 and the specimens (comprising an εPL having an average particle diameter of not more than 50 μm incorporated therein) obtained in Examples 22, 25 and 28.

<<Filler-supported εPL Preparations>>

(Preparation of Filler Preparations)

Filler Preparations 1 to 4

A 25% aqueous solution of εPL and silica gel (SYLYCIA 350, produced by Fuji Silycia Co., Ltd.) were uniformly mixed, and then vacuum-dried at a temperature of 40° C. to obtain the following four filler preparations:

Filler preparations 1:
 εPL: 1.0 parts by weight;
 Silica gel: 9.0 parts by weight
Filler preparations 2:
 εPL: 2.0 parts by weight;
 Silica gel: 8.0 parts by weight
Filler preparations 3:
 εPL: 5.0 parts by weight;
 Silica gel: 5.0 parts by weight
Filler preparations 4:
 Silica gel alone Filler Preparations 5 to 8

A 25% aqueous solution of εPL and zeolite (CS-100, produced by Eishin Kasei K.K.) were uniformly mixed, and then vacuum-dried at a temperature of 40° C. to obtain the following four filler preparations:

Filler preparations 5:
 εPL: 1.0 parts by weight;
 Zeolite: 9.0 parts by weight
Filler preparations 6:
 εPL: 2.0 parts by weight;
 Zeolite: 8.0 parts by weight
Filler preparations 7:
 εPL: 5.0 parts by weight;
 Zeolite: 5.0 parts by weight
Filler preparations 8:
 Zeolite alone Filler Preparations 9 to 12

A 25% aqueous solution of εPL and talc (PK-P, produced by Hayashi Kasei K.K.) were uniformly mixed, and then vacuum-dried at a temperature of 40° C. to obtain the following four filler preparations:

Filler preparations 9:
 εPL: 0.1 parts by weight;
 Talc: 9.9 parts by weight
Filler preparations 10:
 εPL: 0.2 parts by weight;
 Talc: 9.8 parts by weight
Filler preparations 11:
 εPL: 0.5 parts by weight;
 Talc: 9.5 parts by weight
Filler preparations 12:
 Talc alone Filler Preparations 13 to 16

A 25% aqueous solution of εPL and crystalline cellulose (AVICEL PH-101, produced by ASAHI CHEMICAL INDUSTRY, LTD.) were uniformly mixed, and then vacuum-dried at a temperature of 40° C. to obtain the following four filler preparations:

Filler preparations 13:
 εPL: 1.0 parts by weight;
 Crystalline cellulose: 9.0 parts by weight
Filler preparations 14:
 εPL: 2.0 parts by weight;
 Crystalline cellulose: 8.0 parts by weight
Filler preparations 15:
 εPL: 5.0 parts by weight;
 Crystalline cellulose: 5.0 parts by weight
Filler preparations 16:
 Crystalline cellulose alone

εPL-14

εPL-1 was ground by means of a food mill for 30 seconds, and then passed through a wire sieve having a designated dimension of 75 μm defined in JIS Z8801-1987 to obtain εPL-14 in the form of fine powder.

(Moisture Absorption Evaluation Test 1)

Using a microbalance capable of measuring 1/10 mg at minimum, Filler Preparations 1 to 16 and εPL-14 were each precisely measured out in an amount of 5 g. The sample was then allowed to stand in a desiccator which had been kept at a relative humidity of not less than 90% and a temperature of 23° C. for 3 hours. The sample was then again precisely measured out. The percent increase thus measured was defined as moisture absorption of the sample. The results are shown in Table 42 below.

(Test for Evaluation of Powder Condition of Preparations)

Dampened Filler Preparations 1 to 16 and εPL-14 obtained in the above-described moisture absorption evaluation test were then visually observed for powder condition and evaluated in accordance with the following criterion. The results are shown in Table 42 below.

TABLE 42

| Sample Name | Proportion (parts by weight) of εPL and other components in filler preparations | | | | | Moisture absorption % | Judgment of powder condition |
| --- | --- | --- | --- | --- | --- | --- | --- |
| | εPL | Silica gel | Zeolite | Talc | Crystalline cellulose | | |
| Filler Preparations 1 | 1.0 | 9.0 | | | | 12.2 | ⊚ |
| Filler Preparations 2 | 2.0 | 8.0 | | | | 11.5 | ⊚ |
| Filler Preparations 3 | 5.0 | 5.0 | | | | 12.4 | ⊚ |
| Filler Preparations 4 | 0 | 10.0 | | | | 7.9 | ⊚ |
| Filler Preparations 5 | 1.0 | | 9.0 | | | 9.2 | ⊚ |
| Filler Preparations 6 | 2.0 | | 8.0 | | | 9.1 | ⊚ |
| Filler Preparations 7 | 5.0 | | 5.0 | | | 9.7 | ○ |
| Filler Preparations 8 | 0 | | 10.0 | | | 2.9 | ⊚ |
| Filler Preparations 9 | 0.1 | | | 9.9 | | 4.1 | ⊚ |
| Filler Preparations 10 | 0.2 | | | 9.8 | | 3.9 | ⊚ |

TABLE 42-continued

| Sample Name | Proportion (parts by weight) of εPL and other components in filler preparations | | | | Moisture absorption % | Judgment of powder condition |
|---|---|---|---|---|---|---|
| | εPL | Silica gel | Zeolite | Talc | Crystalline cellulose | | |
|---|---|---|---|---|---|---|---|
| Filler Preparations 11 | 0.5 | | | 9.5 | | 4.7 | ⊚ |
| Filler Preparations 12 | 0 | | | 10.0 | | 1.7 | ⊚ |
| Filler Preparations 13 | 1.0 | | | | 9.0 | 10.0 | ⊚ |
| Filler Preparations 14 | 2.0 | | | | 8.0 | 10.7 | ⊚ |
| Filler Preparations 15 | 5.0 | | | | 5.0 | 11.9 | ○ |
| Filler Preparations 16 | 0 | | | | 10.0 | 6.4 | ⊚ |
| εPL-14 | 10.0 | | | | | 9.5 | Δ |

Criterion of evaluation
⊚ : Kept finely divided, no agglomerates observed
○ : Kept finely divided, slight amount of agglomerates developed by moisture absorption observed
Δ: Kept powdery, agglomerates observed in places
×: Much agglomerates developed by moisture absorption observed; not recognized as powder As can be seen in Table 42, Filler Preparations 1 to 16 according to the present invention, though having the same moisture absorption as εPL-14, is little liable to agglomeration and sticking and thus can be kept finely divided even when dampened.

EXAMPLE 82

A polypropylene powder (MFR: 10 g/10 min., 230° C., 21.18 N), BHT and the above-described Filler Preparations 1 were uniformly mixed in a blender in such a manner that the proportion of the polypropylene powder, BHT and Filler Preparations 1 reached 98.9%, 0.1% and 1.0%, respectively. The mixture was then kneaded at an extrusion temperature of 180° C. in a small-sized twin screw extruder produced by Toyo Seiki Seisakusho, Ltd. so that it was pelletized. The pelletized material was then heat-compressed at a temperature of 200° C. and 19.61 MPa in a mold having a size of 50×50×0.5 mm for 1 minute to prepare Polypropylene Sheet-61.

EXAMPLE 83

The procedure of Example 82 was followed except that Filler Preparations 2 was added in an amount of 1.0% instead of Filler Preparations 1 in an amount of 1.0%. As a result, Polypropylene Sheet-62 was prepared.

EXAMPLE 84

The procedure of Example 82 was followed except that Filler Preparations 3 was added in an amount of 1.0% instead of Filler Preparations 1 in an amount of 1.0%. As a result, Polypropylene Sheet-63 was prepared.

Comparative Example 25

The procedure of Example 82 was followed except that Filler Preparations 4 was added in an amount of 1.0% instead of Filler Preparations 1 in an amount of 1.0%. As a result, Polypropylene Sheet-64 was prepared.

EXAMPLE 85

The procedure of Example 82 was followed except that Filler Preparations 5 was added in an amount of 1.0% instead of Filler Preparations 1 in an amount of 1.0%. As a result, Polypropylene Sheet-65 was prepared.

EXAMPLE 86

The procedure of Example 82 was followed except that Filler Preparations 6 was added in an amount of 1.0% instead of Filler Preparations 1 in an amount of 1.0%. As a result, Polypropylene Sheet-66 was prepared.

EXAMPLE 87

The procedure of Example 82 was followed except that Filler Preparations 7 was added in an amount of 1.0% instead of Filler Preparations 1 in an amount of 1.0%. As a result, Polypropylene Sheet-67 was prepared.

Comparative Example 26

The procedure of Example 82 was followed except that Filler Preparations 8 was added in an amount of 1.0% instead of Filler Preparations 1 in an amount of 1.0%. As a result, Polypropylene Sheet-68 was prepared.

EXAMPLE 88

The procedure of Example 82 was followed except that Filler Preparations 9 was added in an amount of 10% instead of Filler Preparations 1 in an amount of 1.0%. As a result, Polypropylene Sheet-69 was prepared.

EXAMPLE 89

The procedure of Example 82 was followed except that Filler Preparations 10 was added in an amount of 10% instead of Filler Preparations 1 in an amount of 1.0%. As a result, Polypropylene Sheet-70 was prepared.

EXAMPLE 90

The procedure of Example 82 was followed except that Filler Preparations 11 was added in an amount of 10% instead of Filler Preparations 1 in an amount of 1.0%. As a result, Polypropylene Sheet-71 was prepared.

Comparative Example 27

The procedure of Example 82 was followed except that Filler Preparations 12 was added in an amount of 1.0% instead of Filler Preparations 1 in an amount of 1.0%. As a result, Polypropylene Sheet-72 was prepared.

EXAMPLE 91

The procedure of Example 82 was followed except that Filler Preparations 13 was added in an amount of 1.0% instead of Filler Preparations 1 in an amount of 1.0%. As a result, Polypropylene Sheet-73 was prepared.

EXAMPLE 92

The procedure of Example 82 was followed except that Filler Preparations 14 was added in an amount of 1.0% instead of Filler Preparations 1 in an amount of 1.0%. As a result, Polypropylene Sheet-74 was prepared.

EXAMPLE 93

The procedure of Example 82 was followed except that Filler Preparations 15 was added in an amount of 1.0% instead of Filler Preparations 1 in an amount of 1.0%. As a result, Polypropylene Sheet-75 was prepared.

Comparative Example 28

The procedure of Example 82 was followed except that Filler Preparations 16 was added in an amount of 1.0% instead of Filler Preparations 1 in an amount of 1.0%. As a result, Polypropylene Sheet-76 was prepared.

EXAMPLE 94

The procedure of Example 82 was followed except that εPL-14 was added in an amount of 0.1% instead of Filler Preparations 1 in an amount of 1.0%. As a result, Polypropylene Sheet-77 was prepared.

EXAMPLE 95

The procedure of Example 82 was followed except that εPL-14 was added in an amount of 0.2% instead of Filler Preparations 1 in an amount of 1.0%. As a result, Polypropylene Sheet-78 was prepared.

EXAMPLE 96

The procedure of Example 82 was followed except that εPL-14 was added in an amount of 0.5% instead of Filler Preparations 1 in an amount of 1.0%. As a result, Polypropylene Sheet-79 was prepared.

Comparative Example 29

The procedure of Example 82 was followed except that neither filler preparations nor εPL powder were. As a result, Polypropylene Sheet-80 was prepared.

(Test 1 for Evaluation of Handleability During Preparation)

The results of evaluation of handleability of Polypropylne Sheet-61 to 80 obtained in Examples 82 to 96 and Comparative Examples 25 to 29 during preparation are shown in Table 43.

(Test 8 for Observation of External Appearance of Sheet)

Polypropylene Sheet-61 to 80 obtained in Examples 82 to 96 and Comparative Examples 25 to 29 were visually observed for external appearance. The results are shown in Table 43 below.

TABLE 43

| Sample Name | Results of evaluation of handleability | Results of evaluation of sheet external appearance — Results of visual evaluation of sheet external appearance | Judgment |
|---|---|---|---|
| Filler Preparations 1 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 2 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 3 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 4 | No agglomeration of filler preparations occurs during granulation. Acceptable handleability is exhibited. | The dispersibility of filler preparations in the sheet and the smoothness of the sheet are extremely good. The sheet is acceptable in external appearance. | |
| Filler Preparations 5 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 6 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 7 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 8 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 9 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 10 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊙ |
| Filler Preparations 11 | No agglomeration of filler preparations occurs during granulation. Acceptable | The dispersibility of filler preparations in the sheet and the smoothness of the sheet are | ⊙ |

TABLE 43-continued

| Sample Name | Results of evaluation of handleability | Results of evaluation of sheet external appearance / Results of visual evaluation of sheet external appearance | Judgment |
|---|---|---|---|
| | handleability is exhibited. | extremely good. The sheet is acceptable in external appearance | |
| Filler Preparations 12 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊚ |
| Filler Preparations 13 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊚ |
| Filler Preparations 14 | No agglomeration of filler preparations occurs during granulation. Acceptable handleability is exhibited. | The dispersibiiity of filler preparations in the sheet and the smoothness of the sheet are extremely good. The sheet is acceptable in external appearance. | ⊚ |
| Filler Preparations 15 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊚ |
| Filler Preparations 16 | No agglomeration of filler preparations occurs during granulation. Acceptable handleability is exhibited. | The dispersibility of filler preparations in the sheet and the smoothness of the sheet are extremely good. The sheet is acceptable in external appearance. | ⊚ |
| εPL powder | Agglomeration and sticking occur during granulation, showing poor handleability | The dispersibility of filler preparations in the sheet and the smoothness of the sheet are extremely good. The sheet is acceptable in external appearance. | ○ |

⊚ : Excellent external sheet appearance; judged applicable in wide application without any problem
○ : Good external sheet appearance; judged applicable in many uses so far as high transparency and smoothness are not required
Δ: Slight poor external sheet appearance; judged difficultly applicable in uses requiring transparency and smoothness but applicable in uses requiring coloring
×: Poor external sheet appearance; judged inapplicable As can be seen in Table 43, the polypropylene sheets comprising filler preparations incorporated therein obtained in Examples 82 to 93 are little liable to sticking or agglomeration during blending and hence exhibit an excellent workability as compared with the polypropylene sheets comprising an εPL powder incorporated therein obtained in Examples 94 to 96.

Further, the polypropylene sheets comprising filler preparations incorporated therein obtained in Examples 82 to 93 exhibit the same external appearance as the polypropylene sheets comprising an εPL powder (water content: 5.5%; average particle diameter: 50 μm) incorporated therein obtained in Examples 94 to 96 and the polypropylene sheets comprising filler alone incorporated therein obtained in Comparative Examples 25 to 28. Thus, these polypropylene sheets show no deterioration of external appearance.

(Antibacterial Effect Test 15)

The procedure of antibacterial effect test 1 was followed except that Polypropylene Sheet-61 to 80 obtained in Examples 82 to 96 and Comparative Examples 25 to 29 were used instead of Polypropylene Sheet-1 and 3 to 14. The results are shown in Table 44 below.

TABLE 44

| Sample No. | | | Proportion (parts by weight) of εPL and other components in filler preparations | | % Added amount of filler preparations | % εPL content in sheet | Difference of increase or loss | |
|---|---|---|---|---|---|---|---|---|
| | P.P. Sheet No. | Preparations | εPL | Filler | | | Not washed | Washed with flowing water for 30 min. |
| Example 82 | 61 | Silica gel-supported εPL | 1.0 | 9.0 | 1.0 | 0.1 | 7.2 | 6.1 |
| Example 83 | 62 | Silica gel-supported εPL | 2.0 | 8.0 | 1.0 | 0.2 | 7.2 | 7.0 |
| Example 84 | 63 | Silica gel-supported εPL | 5.0 | 5.0 | 1.0 | 0.5 | 7.2 | 7.2 |
| Comparative Example 25 | 64 | Silica gel alone | 0 | 10 | 1.0 | 0 | 0 | 0 |
| Example 85 | 65 | Zeolite-supported εPL | 1.0 | 9.0 | 1.0 | 0.1 | 7.2 | 5.5 |
| Example 86 | 66 | Zeolite-supported εPL | 2.0 | 8.0 | 1.0 | 0.2 | 7.2 | 7.1 |
| Example 87 | 67 | Zeolite-supported εPL | 5.0 | 5.0 | 1.0 | 0.5 | 7.2 | 7.2 |
| Comparative Example 26 | 68 | Zeolite alone | 0 | 10 | 10.0 | 0 | 0 | 0 |
| Example 88 | 69 | Talc-supported εPL | 0.1 | 9.9 | 10.0 | 0.1 | 7.2 | 6.2 |

TABLE 44-continued

| Sample No. | | | Proportion (parts by weight) of εPL and other components in filler preparations | | % Added amount of filler preparations | % εPL content in sheet | Difference of increase or loss | |
|---|---|---|---|---|---|---|---|---|
| | P.P. Sheet No. | Preparations | εPL | Filler | | | Not washed | Washed with flowing water for 30 min. |
| Example 89 | 70 | Talc-supported εPL | 0.2 | 9.8 | 10.0 | 0.2 | 7.2 | 7.2 |
| Example 90 | 71 | Talc-supported εPL | 0.5 | 9.5 | 10.0 | 0.5 | 7.2 | 7.2 |
| Comparative Example 27 | 72 | Talc alone | 0 | 10 | 1.0 | 0 | 0 | 0 |
| Example 91 | 73 | Cellulose-supported εPL | 1.0 | 9.0 | 1.0 | 0.1 | 7.2 | 5.0 |
| Example 92 | 74 | Cellulose-supported εPL | 2.0 | 8.0 | 1.0 | 0.2 | 7.2 | 7.2 |
| Example 93 | 75 | Cellulose-supported εPL | 5.0 | 5.0 | 1.0 | 0.5 | 7.2 | 7.2 |
| Comparative Example 28 | 76 | Crystalline cellulose alone | 0 | 10 | 1.0 | 0 | 0 | 0 |
| Example 94 | 77 | εPL-14 | 10 | 0 | 0.1 | 0.1 | 7.2 | 5.2 |
| Example 95 | 78 | εPL-14 | 10 | 0 | 0.2 | 0.2 | 7.2 | 7.0 |
| Example 96 | 79 | εPL-14 | 10 | 0 | 0.5 | 0.5 | 7.2 | 7.2 |
| Comparative Example 29 | 80 | None | | | 0 | 0 | 0 | 0 |

Name of bacterial: *Escherichia coli* (IFO3972)

As can be seen in Table 44, the polypropylene sheets (comprising a filler incorporated therein) obtained in Examples 82 to 93 show no significant difference in antibacterial effect on *Escherichia coli* with both unwashed specimen and washed specimen from the polypropylene sheets (comprising an εPL having a water content of 5.5% and an average particle diameter of 50 μm incorporated therein) obtained in Examples 94 to 96, demonstrating that they show no drop of antibacterial effect due to supposition of εPL on filler.

(Antibacterial Effect Test 16)

The procedure of antibacterial effect test 2 was followed except that Polypropylene Sheet-61 to 80 obtained in Examples 82 to 96 and Comparative Examples 25 to 29 were used instead of Polypropylene Sheet-1 and 3 to 14. The results are shown in Table 45 below.

TABLE 45

| Sample No. | | | Proportion (parts by weight) of εPL and other components in filler preparations | | % Added amount of filler preparations | % εPL content in sheet | Difference of increase or loss | |
|---|---|---|---|---|---|---|---|---|
| | P.P. Sheet No. | Preparations | εPL | Filler | | | Not washed | Washed with flowing water for 30 min. |
| Example 82 | 61 | Silica gel-supported εPL | 1.0 | 9.0 | 1.0 | 0.1 | 7.2 | 6.3 |
| Example 83 | 62 | Silica gel-supported εPL | 2.0 | 8.0 | 1.0 | 0.2 | 7.2 | 7.2 |
| Example 84 | 63 | Silica gel-supported εPL | 5.0 | 5.0 | 1.0 | 0.5 | 7.2 | 7.2 |
| Comparative Example 25 | 64 | Silica gel alone | 0 | 10 | 1.0 | 0 | 0 | 0 |
| Example 85 | 65 | Zeolite-supported εPL | 1.0 | 9.0 | 1.0 | 0.1 | 7.2 | 5.8 |
| Example 86 | 66 | Zeolite-supported εPL | 2.0 | 8.0 | 1.0 | 0.2 | 7.2 | 6.8 |
| Example 87 | 67 | Zeolite-supported εPL | 5.0 | 5.0 | 1.0 | 0.5 | 7.2 | 7.2 |
| Comparative Example 26 | 68 | Zeolite alone | 0 | 10 | 10.0 | 0 | 0 | 0 |
| Example 88 | 69 | Talc-supported εPL | 0.1 | 9.9 | 10.0 | 0.1 | 7.2 | 6.3 |
| Example 89 | 70 | Talc-supported εPL | 0.2 | 9.8 | 10.0 | 0.2 | 7.2 | 7.0 |
| Example 90 | 71 | Talc-supported εPL | 0.5 | 9.5 | 10.0 | 0.5 | 7.2 | 7.2 |
| Comparative Example 27 | 72 | Talc alone | 0 | 10 | 1.0 | 0 | 0 | 0 |
| Example 91 | 73 | Cellulose-supported εPL | 1.0 | 9.0 | 1.0 | 0.1 | 7.2 | 5.2 |
| Example 92 | 74 | Cellulose-supported εPL | 2.0 | 8.0 | 1.0 | 0.2 | 7.2 | 7.0 |
| Example 93 | 75 | Cellulose-supported εPL | 5.0 | 5.0 | 1.0 | 0.5 | 7.2 | 7.2 |
| Comparative Example 28 | 76 | Crystalline cellulose alone | 0 | 10 | 1.0 | 0 | 0 | 0 |
| Example 94 | 77 | εPL-14 | 10 | 0 | 0.1 | 0.1 | 7.2 | 5.5 |
| Example 95 | 78 | εPL-14 | 10 | 0 | 0.2 | 0.2 | 7.2 | 7.2 |
| Example 96 | 79 | εPL-14 | 10 | 0 | 0.5 | 0.5 | 7.2 | 7.2 |
| Comparative Example 29 | 80 | None | | | 0 | 0 | 0 | 0 |

Name of bacterial: *Staphylococcus aureus* (IFO12732)

As can be seen in Table 45, the polypropylene sheets (comprising a filler incorporated therein) obtained in Examples 82 to 93 show no significant difference in antibacterial effect on *Staphylococcus aureus* with both unwashed specimen and washed specimen from the polypropylene sheets (comprising an εPL having a water content of 5.5% and an average particle diameter of 50 μm incorporated therein) obtained in Examples 94 to 96, demonstrating that they show no drop of antibacterial effect due to supposition of εPL on filler.

EXAMPLE 97

The procedure of Example 10 was followed except that Filler Preparations 1 was added in an amount of 1.0% instead of εPL-1 in an amount of 1.0%. As a result, Unsaturated Polyester Sheet-46 was prepared.

EXAMPLE 98

The procedure of Example 10 was followed except that Filler Preparations 2 was added in an amount of 1.0% instead of εPL-1 in an amount of 1.0%. As a result, Unsaturated Polyester Sheet-47 was prepared.

EXAMPLE 99

The procedure of Example 10 was followed except that Filler Preparations 3 was added in an amount of 1.0% instead of εPL-1 in an amount of 1.0%. As a result, Unsaturated Polyester Sheet-48 was prepared.

Comparative Example 30

The procedure of Example 10 was followed except that Filler Preparations 4 was added in an amount of 1.0% instead of εPL-1 in an amount of 1.0%. As a result, Unsaturated Polyester Sheet-49 was prepared.

EXAMPLE 100

The procedure of Example 10 was followed except that Filler Preparations 5 was added in an amount of 1.0% instead of εPL-1 in an amount of 1.0%. As a result, Unsaturated Polyester Sheet-50 was prepared.

EXAMPLE 101

The procedure of Example 10 was followed except that Filler Preparations 6 was added in an amount of 1.0% instead of εPL-1 in an amount of 1.0%. As a result, Unsaturated Polyester Sheet-51 was prepared.

EXAMPLE 102

The procedure of Example 10 was followed except that Filler Preparations 7 was added in an amount of 1.0% instead of εPL-1 in an amount of 1.0%. As a result, Unsaturated Polyester Sheet-52 was prepared.

Comparative Example 31

The procedure of Example 10 was followed except that Filler Preparations 8 was added in an amount of 1.0% instead of εPL-1 in an amount of 1.0%. As a result, Unsaturated Polyester Sheet-53 was prepared.

EXAMPLE 103

The procedure of Example 10 was followed except that Filler Preparations 6 was added in an amount of 10% instead of εPL-1 in an amount of 1.0%. As a result, Unsaturated Polyester Sheet-54 was prepared.

EXAMPLE 104

The procedure of Example 10 was followed except that Filler Preparations 6 was added in an amount of 10% instead of εPL-1 in an amount of 1.0%. As a result, Unsaturated Polyester Sheet-55 was prepared.

EXAMPLE 105

The procedure of Example 10 was followed except that Filler Preparations 7 was added in an amount of 10% instead of εPL-1 in an amount of 1.0%. As a result, Unsaturated Polyester Sheet-56 was prepared.

Comparative Example 32

The procedure of Example 10 was followed except that Filler Preparations 8 was added in an amount of 10% instead of εPL-1 in an amount of 1.0%. As a result, Unsaturated Polyester Sheet-57 was prepared.

EXAMPLE 106

The procedure of Example 10 was followed except that Filler Preparations 9 was added in an amount of 1.0% instead of εPL-1 in an amount of 1.0%. As a result, Unsaturated Polyester Sheet-58 was prepared.

EXAMPLE 107

The procedure of Example 10 was followed except that Filler Preparations 10 was added in an amount of 1.0% instead of εPL-1 in an amount of 1.0%. As a result, Unsaturated Polyester Sheet-59 was prepared.

EXAMPLE 108

The procedure of Example 10 was followed except that Filler Preparations 11 was added in an amount of 1.0% instead of εPL-1 in an amount of 1.0%. As a result, Unsaturated Polyester Sheet-60 was prepared.

Comparative Example 33

The procedure of Example 10 was followed except that Filler Preparations 12 was added in an amount of 1.0% instead of εPL-1 in an amount of 1.0%. As a result, Unsaturated Polyester Sheet-61 was prepared.

EXAMPLE 109

The procedure of Example 10 was followed except that εPL-14 was added in an amount of 0.1% instead of εPL-1 in an amount of 1.0%. As a result, Unsaturated Polyester Sheet-62 was prepared.

EXAMPLE 110

The procedure of Example 10 was followed except that εPL-14 was added in an amount of 0.2% instead of εPL-1 in an amount of 1.0%. As a result, Unsaturated Polyester Sheet-63 was prepared.

EXAMPLE 111

The procedure of Example 10 was followed except that εPL-14 was added in an amount of 0.5% instead of εPL-1 in an amount of 1.0%. As a result, Unsaturated Polyester Sheet-64 was prepared.

(Test 2 for Evaluation of Handleability During Preparation)
The results of evaluation of handleability of Unsaturated Polyester Sheet-46 to 64 obtained in Examples 97 to 111 and Comparative Examples 30 to 33 during preparation are shown in Table 46.

(Test 9 for Observation of External Appearance of Sheet)
Unsaturated Polyester Sheet-46 to 64 obtained in Examples 97 to 111 and Comparative Examples 30 to 33 were visually observed for external appearance. The results are shown in Table 46 below.

TABLE 46

| Sample Name | Results of evaluation of handleability | Results of evaluation of sheet external appearance<br>Results of visual evaluation of sheet external appearance | Judgment |
|---|---|---|---|
| Filler Preparations 1 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 2 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 3 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 4 | No agglomeration of filler preparations occurs during sheet formation. Acceptable handleability is exhibited. | The dispersibility of filler preparations in the sheet and the smoothness of the sheet are extremely good. The sheet is acceptable in external appearance. | |
| Filler Preparations 5 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 6 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 7 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 8 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 9 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 10 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 11 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 12 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 13 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 14 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 15 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |
| Filler Preparations 16 | No agglomeration of filler preparations occurs during sheet formation. Acceptable handleability is exhibited. | The dispersibility of filler preparations in the sheet and the smoothness of the sheet are extremely good. The sheet is acceptable in external appearance. | ⊚ |

TABLE 46-continued

| Sample Name | Results of evaluation of handleability | Results of evaluation of sheet external appearance / Results of visual evaluation of sheet external appearance | Judgment |
|---|---|---|---|
| εPL-14 | Agglomeration and sticking occur during sheet formation, showing poor handleability. | The dispersibility of filler preparations in the sheet and the smoothness of the sheet are extremely good. The sheet is acceptable in external appearance. | ◯ |

◉ : Excellent external sheet appearance; judged applicable in wide application without any problem
◯ : Good external sheet appearance; judged applicable in many uses so far as high transparency and smoothness are not required
Δ: Slight poor external sheet appearance; judged difficultly applicable in uses requiring transparency and smoothness but applicable in uses requiring coloring
×: Poor external sheet appearance; judged inapplicable
◉: Excellent external sheet appearance; judged applicable in wide application without any problem
◯ : Good external sheet appearance; judged applicable in many uses so far as high transparency and smoothness are not required
Δ: Slight poor external sheet appearance; judged difficultly applicable in uses requiring transparency and smoothness but applicable in uses requiring coloring
×: Poor external sheet appearance; judged inapplicable As can be seen in Table 46, the unsaturated polyester sheets comprising filler preparations incorporated therein obtained in Examples 97 to 108 are little liable to sticking or agglomeration during blending and hence exhibit an excellent workability as compared with the unsaturated polyester sheets comprising an εPL powder incorporated therein obtained in Examples 109 to 111.

Further, the unsaturated polyester sheets comprising filler preparations incorporated therein obtained in Examples 97 to 108 exhibit the same external appearance as the unsaturated polyester sheets comprising an εPL powder incorporated therein obtained in Examples 109 to 111 and the unsaturated polyester sheets comprising filler alone incorporated therein obtained in Comparative Examples 30 to 33. Thus, these unsaturated polyester sheets show no deterioration of external appearance.

(Antibacterial Effect Test 17)

The procedure of antibacterial effect test 1 was followed except that Unsaturated Polyester Sheet-14 and 46 to 64 obtained in Examples 97 to 111 and Comparative Examples 10 and 30 to 33 were used instead of Polypropylene Sheet-1 and 3 to 14. The results are shown in Table 47 below.

TABLE 47

| Sample Name | | | Proportion (parts by weight) of εPL and other components in filler preparations | | % Added amount of filler | % εPL content in sheet | Difference of increase or loss | |
|---|---|---|---|---|---|---|---|---|
| | U.P. Sheet No. | Preparations | εPL | Filler | preparations | | Not washed | Washed with flowing water for 30 min. |
| Example 97 | 46 | Silica gel-supported εPL | 1.0 | 9.0 | 1.0 | 0.1 | 7.3 | 5.9 |
| Example 98 | 47 | Silica gel-supported εPL | 2.0 | 8.0 | 1.0 | 0.2 | 7.3 | 7.0 |
| Example 99 | 48 | Silica gel-supported εPL | 5.0 | 5.0 | 1.0 | 0.5 | 7.3 | 7.3 |
| Comparative Example 30 | 49 | Silica gel alone | 0 | 10 | 1.0 | 0 | 0 | 0 |
| Example 100 | 50 | Zeolite-supported εPL | 1.0 | 9.0 | 1.0 | 0.1 | 7.1 | 5.0 |
| Example 101 | 51 | Zeolite-supported εPL | 2.0 | 8.0 | 1.0 | 0.2 | 7.3 | 7.1 |
| Example 102 | 52 | Zeolite-supported εPL | 5.0 | 5.0 | 1.0 | 0.5 | 7.3 | 7.3 |
| Comparative Example 31 | 53 | Zeolite alone | 0 | 10 | 10.0 | 0 | 0 | 0 |
| Example 103 | 54 | Talc-supported εPL | 0.1 | 9.9 | 10.0 | 0.1 | 7.3 | 6.2 |
| Example 104 | 55 | Talc-supported εPL | 0.2 | 9.8 | 10.0 | 0.2 | 7.3 | 7.3 |
| Example 105 | 56 | Talc-supported εPL | 0.5 | 9.5 | 10.0 | 0.5 | 7.3 | 7.3 |
| Comparative Example 32 | 57 | Talc alone | 0 | 10 | 1.0 | 0 | 0 | 0 |
| Example 106 | 58 | Cellulose-supported εPL | 1.0 | 9.0 | 1.0 | 0.1 | 7.3 | 5.5 |
| Example 107 | 59 | Cellulose-supported εPL | 2.0 | 8.0 | 1.0 | 0.2 | 7.3 | 7.3 |
| Example 108 | 60 | Cellulose-supported εPL | 5.0 | 5.0 | 1.0 | 0.5 | 7.3 | 7.3 |
| Comparative Example 33 | 61 | Crystalline cellulose alone | 0 | 10 | 1.0 | 0 | 0 | 0 |
| Example 109 | 62 | εPL-14 | 10 | 0 | 0.1 | 0.1 | 7.3 | 5.2 |
| Example 110 | 63 | εPL-14 | 10 | 0 | 0.2 | 0.2 | 7.3 | 7.3 |
| Example 111 | 64 | εPL-14 | 10 | 0 | 0.5 | 0.5 | 7.3 | 7.3 |
| Comparative Example 10 | 14 | None | | | | 0 | 0 | 0 |

Name of bacterial: *Escherichia coli* (IFO3972)

As can be seen in Table 47, the unsaturated polyester sheets (comprising a filler incorporated therein) obtained in Examples 97 to 108 show no significant difference in antibacterial effect on *Escherichia coli* with both unwashed specimen and washed specimen from the unsaturated polyester sheets (comprising an εPL having a water content of 5.5% and an average particle diameter of 50 μm incorporated therein) obtained in Examples 109 to 111, demonstrating that they show no drop of antibacterial effect due to supposition of εPL on filler.

(Antibacterial Effect Test 18)

The procedure of antibacterial effect test 2 was followed except that Unsaturated Polyester Sheet-14 and 46 to 64 obtained in Examples 97 to 111 and Comparative Examples 10 and 30 to 33 were used instead of Polypropylene Sheet-1 and 3 to 14. The results are shown in Table 48 below.

TABLE 48

| Sample Name | | U.P. Sheet No. | Preparations | Proportion (parts by weight) of εPL and other components in filler preparations | | % Added amount of filler preparations | % εPL content in sheet | Difference of increase or loss | |
|---|---|---|---|---|---|---|---|---|---|
| | | | | εPL | Filler | | | Not washed | Washed with flowing water for 30 min. |
| Example 97 | | 46 | Silica gel-supported εPL | 1.0 | 9.0 | 1.0 | 0.1 | 7.3 | 5.3 |
| Example 98 | | 47 | Silica gel-supported εPL | 2.0 | 8.0 | 1.0 | 0.2 | 7.3 | 6.2 |
| Example 99 | | 49 | Silica gel-supported εPL | 5.0 | 5.0 | 1.0 | 0.5 | 7.3 | 7.3 |
| Comparative Example 30 | | 50 | Silica gel alone | 0 | 10 | 1.0 | 0 | 0 | 0 |
| Example 100 | | 51 | Zeolite-supported εPL | 1.0 | 9.0 | 1.0 | 0.1 | 7.3 | 5.5 |
| Example 101 | | 56 | Zeolite-supported εPL | 2.0 | 8.0 | 1.0 | 0.2 | 7.3 | 6.5 |
| Example 102 | | 57 | Zeolite-supported εPL | 5.0 | 5.0 | 1.0 | 0.5 | 7.3 | 7.3 |
| Comparative Example 31 | | 58 | Zeolite alone | 0 | 10 | 10.0 | 0 | 0 | 0 |
| Example 103 | | 59 | Talc-supported εPL | 0.1 | 9.9 | 10.0 | 0.1 | 7.3 | 7.3 |
| Example 104 | | 60 | Talc-supported εPL | 0.2 | 9.8 | 10.0 | 0.2 | 7.3 | 7.3 |
| Example 105 | | 61 | Talc-supported εPL | 0.5 | 9.5 | 10.0 | 0.5 | 7.3 | 7.3 |
| Comparative Example 32 | | 62 | Talc alone | 0 | 10 | 1.0 | 0 | 0 | 0 |
| Example 106 | | 63 | Cellulose-supported εPL | 1.0 | 9.0 | 1.0 | 0.1 | 7.3 | 7.3 |
| Example 107 | | 64 | Cellulose-supported εPL | 2.0 | 8.0 | 1.0 | 0.2 | 7.3 | 7.3 |
| Example 108 | | 14 | Cellulose-supported εPL | 5.0 | 5.0 | 1.0 | 0.5 | 7.3 | 7.3 |
| Comparative Example 33 | | 76 | Crystalline cellulose alone | 0 | 10 | 1.0 | 0 | 0 | 0 |
| Example 109 | | 77 | εPL-14 | 10 | 0 | 0.1 | 0.1 | 7.3 | 5.0 |
| Example 110 | | 78 | εPL-14 | 10 | 0 | 0.2 | 0.2 | 7.3 | 6.2 |
| Example 111 | | 79 | εPL-14 | 10 | 0 | 0.5 | 0.5 | 7.3 | 7.3 |
| Comparative Example 10 | | 80 | None | | | 0 | 0 | 0 | 0 |

Name of bacterial: *Staphylococcus aureus* (IFO12732)

As can be seen in Table 48, the unsaturated polyester sheets (comprising a filler incorporated therein) obtained in Examples 97 to 108 show no significant difference in antibacterial effect on *Staphylococcus aureus* with both unwashed specimen and washed specimen from the unsaturated polyester sheets (comprising an εPL having a water content of 5.5% and an average particle diameter of 50 μm incorporated therein) obtained in Examples 109 to 111, demonstrating that they show no drop of antibacterial effect due to supposition of εPL on filler.

INDUSTRIAL APPLICABILITY

The antibacterial resin composition according to the present invention exhibits an excellent antibacterial capacity. Further, the antibacterial resin composition according to the present invention comprises ε-polylysine or salt thereof (εPL), which is commonly used as a food preservative, incorporated therein as an antibacterial agent and thus has an extremely small adverse effect on the human body and is safe. Moreover, the antibacterial resin composition according to the present invention comprises an εPL agent having a small water content incorporated therein and thus can be used for materials having a low hydrophilicity. Further, since the εPL agent can be fairly dispersed in the resin, the resulting antibacterial resin-molded article exhibits is not liable to destruction of external appearance and is excellent in resistance to washing. Accordingly, the antibacterial resin composition of the present invention can find good and wide application in medical sanitary goods, tableware, daily necessaries, automobile interior material, household appliance, film, sheet, fiber, coating compound such as paint, ink, and other goods which must be antibacterial. Further, the molded articles obtained from the resin composition according to the present invention can maintain its antibacterial effect even after repeated use and thus can be used over an extended period of time.

What is claimed is:

1. An antibacterial resin composition comprising:

a synthetic resin; and an ε-polylysine or ε-polylysine salt composition incorporated in said synthetic resin, wherein said ε-polylysine or ε-polylysine salt composition comprises an ε-polylysine or ε-polylysine salt supported on a carrier, wherein said ε-polylysine or ε-polylysine salt composition has a water content of not more than 15% by weight and is obtained by a process which comprises subjecting an aqueous solution containing ε-polylysine or salt thereof to azeotropic treatment in the presence of an azeotropic agent to undergo dehydration followed by drying, and wherein said resin composition has a water content of not more than 15% by weight.

2. The antibacterial resin composition according to claim 1, further comprising a surface active agent incorporated therein.

3. The antibacterial resin composition according to claim 2, wherein the mixing ratio of said ϵ-polylysine or ϵ-polylysine salt and said surface active agent is from 9:1 to 1:9 by weight.

4. The antibacterial resin composition according to claim 2, wherein said ϵ-polylysine or ϵ-polylysine salt is incorporated therein in admixture with said surface active agent.

5. The antibacterial resin composition according to claim 3, wherein said ϵ-polylysine or ϵ-polylysine salt is incorporated therein in admixture with said surface active agent.

6. The antibacterial resin composition according to claim 1, further comprising a dispersant incorporated therein.

7. The antibacterial resin composition according to claim 6, wherein the mixing ratio of said ϵ-polylysine or ϵ-polylysine salt and said dispersant is from 100:1 to 1:100 by weight.

8. The antibacterial resin composition according to claim 2, further comprising a dispersant incorporated therein.

9. The antibacterial resin composition according to claim 8, wherein the mixing ratio of said ϵ-polylysine or ϵ-polylysine salt and said dispersant is from 100:1 to 1:100 by weight.

10. The antibacterial resin composition according to claim 1, wherein said ϵ-polylysine or ϵ-polylysine salt has an average particle diameter of not more than 200 μm.

11. The antibacterial resin composition according to claim 1, wherein the content of said ϵ-polylysine or ϵ-polylysine salt in said composition is from 0.001 to 10% by weight.

12. A molded article obtained using an antibacterial resin composition according to claim 1.

13. A molded article obtained using an antibacterial resin composition according to claim 2.

14. A molded article obtained using an antibacterial resin composition according to claim 3.

15. A molded article obtained using an antibacterial resin composition according to claim 4.

16. A molded article obtained using an antibacterial resin composition according to claim 5.

17. A molded article obtained using an antibacterial resin composition according to claim 6.

18. A molded article obtained using an antibacterial resin composition according to claim 7.

19. A molded article obtained using an antibacterial resin composition according to claim 8.

20. A molded article obtained using an antibacterial resin composition according to claim 9.

21. A molded article obtained using an antibacterial resin composition according to claim 10.

22. A molded article obtained using an antibacterial resin composition according to claim 11.

* * * * *